(12) United States Patent
Kimrey, Jr. et al.

(10) Patent No.: US 11,202,349 B2
(45) Date of Patent: Dec. 14, 2021

(54) VESSELS FOR ARTICLE HEATING SYSTEMS

(71) Applicant: 915 Labs, Inc., Denver, CO (US)

(72) Inventors: Harold Dail Kimrey, Jr., Knoxville, TN (US); Samuel Dean Giles, Knoxville, TN (US); James Austin Ridgell, Knoxville, TN (US)

(73) Assignee: 915 LABS, INC., Denver, CO (US)

( * ) Notice: Subject to any disclaimer, the term of this patent is extended or adjusted under 35 U.S.C. 154(b) by 340 days.

(21) Appl. No.: 16/165,654

(22) Filed: Oct. 19, 2018

(65) Prior Publication Data

US 2019/0124730 A1 Apr. 25, 2019

Related U.S. Application Data

(60) Provisional application No. 62/574,596, filed on Oct. 19, 2017, provisional application No. 62/574,588, (Continued)

(51) Int. Cl.
*H05B 6/80* (2006.01)
*H05B 6/78* (2006.01)
(Continued)

(52) U.S. Cl.
CPC .............. *H05B 6/802* (2013.01); *A23L 3/01* (2013.01); *A23L 3/02* (2013.01); *A61L 2/04* (2013.01);
(Continued)

(58) Field of Classification Search
CPC ......... G06F 2205/123; G06F 2209/521; G06F 5/12; G06F 9/526; A23L 3/01; A23L 3/02;
(Continued)

(56) References Cited

U.S. PATENT DOCUMENTS

| 8,586,899 B2 * | 11/2013 | Mackay | B65G 33/06 |
| | | | 219/700 |
| 2001/0051202 A1 * | 12/2001 | Hofer | A21B 3/04 |
| | | | 426/523 |

(Continued)

FOREIGN PATENT DOCUMENTS

| GB | 1063877 A | 3/1967 |
| WO | 2005023013 A1 | 3/2005 |

(Continued)

OTHER PUBLICATIONS

International Searching Authority, International Search Report and Written Opinion, issued for International Application No. PCT/US2018/056745, dated Feb. 15, 2019 (18 pages).

*Primary Examiner* — Quang T Van
(74) *Attorney, Agent, or Firm* — Polsinelli PC

(57) ABSTRACT

Systems and processes for use in heating articles include passing a carrier loaded with an article through a vessel inlet and into a first vessel portion and moving the loaded carrier in a first direction through the first vessel portion away from the inlet. During at least a portion of the movement through the first vessel portion, the article is contacted with a first fluid medium. The loaded carrier is moved carrier in a second direction opposite the first direction through a second vessel portion toward a vessel outlet. During at least a portion of the movement through the second vessel portion, the articles is contacted with a second fluid medium. In certain implementations, each of the first direction and the second direction are vertical.

20 Claims, 14 Drawing Sheets

Related U.S. Application Data filed on Oct. 19, 2017, provisional application No. 62/574,601, filed on Oct. 19, 2017.

(51) Int. Cl.
| | |
|---|---|
| *A23L 3/01* | (2006.01) |
| *H05B 6/70* | (2006.01) |
| *A23L 3/02* | (2006.01) |
| *A61L 2/04* | (2006.01) |
| *F27B 5/14* | (2006.01) |
| *F27B 5/06* | (2006.01) |

(52) U.S. Cl.
CPC ............... *H05B 6/701* (2013.01); *H05B 6/78* (2013.01); *H05B 6/782* (2013.01); *H05B 6/784* (2013.01); *H05B 6/80* (2013.01); *A61L 2202/21* (2013.01); *A61L 2202/24* (2013.01); *F27B 5/14* (2013.01); *F27B 2005/062* (2013.01); *H05B 2206/045* (2013.01)

(58) Field of Classification Search
CPC .... A61L 2202/21; A61L 2202/24; A61L 2/04; F27B 2005/062; F27B 5/14; H05B 2206/045; H05B 6/701; H05B 6/78; H05B 6/782; H05B 6/784; H05B 6/80; H05B 6/802
USPC ....... 219/687, 688, 689, 690, 679, 695, 700, 219/710, 757; 435/34, 286.5, 287.3, 435/287.2; 422/130, 400; 705/37; 426/241, 523

See application file for complete search history.

(56) References Cited

U.S. PATENT DOCUMENTS

| | | |
|---|---|---|
| 2010/0126988 A1 | 5/2010 | Mackay et al. |
| 2016/0029685 A1* | 2/2016 | Tang ...................... H05B 6/802 426/241 |
| 2017/0311634 A1 | 11/2017 | Kimrey, Jr. et al. |

FOREIGN PATENT DOCUMENTS

| | | |
|---|---|---|
| WO | 2013138455 A1 | 9/2013 |
| WO | 2015171763 A1 | 11/2015 |

\* cited by examiner

VESSELS FOR ARTICLE HEATING SYSTEMS

CROSS-REFERENCE TO RELATED APPLICATIONS

This application is related to and claims priority under 35 U.S.C. § 119(e) from U.S. Patent Application No. 62/574,588, filed Oct. 19, 2017, titled "MICROWAVE HEATING SYSTEM WITH ENHANCED TEMPERATURE CONTROL"; U.S. Patent Application No. 62/574,596, filed Oct. 19, 2017, titled "MODULAR MICROWAVE HEATING SYSTEM"; and U.S. Patent Application No. 62/574,601, filed Oct. 19, 2017, titled "MICROWAVE HEATING SYSTEM INCLUDING SPLIT CHAMBER VESSELS", the entire contents of which are incorporated by reference for all purposes.

TECHNICAL FIELD

Aspects of the present disclosure are directed to heating systems in which articles are heated, at least in part, by exposure to microwave energy. In particular, the present disclosure is directed to vessels for use in at least one of heating, cooling, or maintaining the temperature of the articles.

BACKGROUND

Microwave energy has been used as a source of energy to rapidly and effectively heat articles in many different applications. Because of its ability to quickly and thoroughly heat an article, microwave energy in particular may be employed in specific applications where the rapid achievement of a prescribed minimum temperature is desirable, such as, for example, pasteurization or sterilization processes. Additionally, because microwave energy is generally volumetric, it may be useful for heating many dielectrically and thermally sensitive articles, such as food and pharmaceuticals. However, to date, the complexities and nuances of safely and effectively applying microwave energy, particularly on a commercial scale, have severely limited its application in rapid thermal processing. Accordingly, a need exists for efficient and cost-effective industrial scale microwave energy heating systems suitable for use in a wide variety of end-use applications.

SUMMARY

In one aspect of the present disclosure, a process for heating articles in a heating system is provided, the process includes passing an article in a carrier through a heating chamber that is at least partially filled with a liquid medium to form a liquid bath. The process further includes heating the article in the carrier, wherein the article is at least partially submerged in the liquid bath during the heating, and wherein at least a portion of the heating is performed using microwave energy. The process also includes one or more of adding fluid into and removing fluid from at least one location in the heating chamber to maintain a temperature profile across the heating chamber in which a temperature of the liquid bath at an inlet area of the heating chamber is at least 10° C. cooler than a temperature of the liquid bath at an outlet area of the heating chamber.

In another aspect of the present disclosure, a heating system for heating articles is provided. The heating system includes a heating chamber for heating articles using microwave energy, the heating chamber configured to be at least partially filled with a fluid forming a liquid bath. The heating system further includes a fluid distribution and temperature control system. The fluid distribution and temperature control system includes at least one heat transfer device for one or more of heating and cooling the fluid and nozzles for one or more of discharging fluid into the heating chamber and removing fluid from the heating chamber. The nozzles are in fluid flow communication with the heat transfer device and are spaced apart from one another along a length of the heating chamber.

In still another aspect of the present disclosure, a process for heating articles includes sequentially passing loaded carriers in a continuous manner through a first processing section and sequentially passing said plurality of loaded carriers in an incremental manner through a second processing section using an incremental convey segment. The incremental convey segment includes sequential carrier-receiving slots, each carrier-receiving slot configured to receive one of said loaded carriers and the incremental convey segment is configured to be moved incrementally at multiples of discrete intervals corresponding to the carrier-receiving slots. The process further includes sequentially passing the loaded carriers in a continuous manner through a third processing section and heating articles supported by the carriers with microwave energy in at least one of said first, second, and third processing sections, the heating of the articles occurring while the articles are submerged in a liquid bath and at a pressure greater than atmospheric pressure.

In yet another aspect of the present disclosure, a process for heating articles in a heating system is provided. The process includes passing a first carrier loaded with an article through a first processing section using a first convey segment, the first loaded carrier having a first residence time in said first processing section of $\tau_1$. The process further includes transferring the first loaded carrier from the first convey segment to a vertical convey segment, the transferring including loading the first loaded carrier into a carrier slot of the vertical convey segment. The loaded carrier is passed through a second processing section using the vertical convey segment by incrementally actuating the vertical convey segment to move the first loaded carrier vertically such that the first loaded carrier has a residence time in said second processing section of $\tau_2$. The process further includes transferring the loaded carrier from the vertical convey segment to a third convey segment, wherein the transferring includes removing the first loaded carrier from the carrier slot of the vertical convey segment. The process also includes transporting a second loaded carrier through the first and the second processing sections by repeating each of the previously described steps.

In another aspect of the present disclosure, a heating system for heating a plurality of articles is provided. The system includes a heating chamber for heating an article in a carrier using microwave energy, a cooling chamber for cooling the article in the carrier, and a holding chamber disposed between the heating chamber and the cooling chamber. The heating chamber is adapted to be at least partially filled with a heating chamber fluid medium and the cooling chamber is adapted to be at least partially filled with a cooling chamber fluid medium.

In another aspect of the present disclosure heating system for heating articles is provided. The heating system includes a heating chamber for heating using microwave energy, the heating chamber configured to be at least partially filled with fluid medium. The heating system further includes a conveyor system for transporting a carrier holding an article in a convey direction through the heating chamber. The conveyor system includes at least two spaced apart convey segments disposed within the heating chamber, and the convey segments are spaced apart from one another in the convey direction.

In still another aspect of the present disclosure, a process for heating articles in a heating system is provided. The process includes introducing a carrier supporting an article into a heating chamber, the article being at least partially submerged in a liquid bath in the heating chamber. The method further includes passing the carrier by a first microwave launcher along a first convey segment in a convey direction. During at least a portion of the passing by the first microwave launcher, microwave energy is discharged from the first microwave launcher toward the article in the carrier. The process further includes passing the carrier by a second microwave launcher along a second convey segment in said convey direction. During at least a portion of the passing by the second microwave launcher, microwave energy is discharged from the second microwave launcher toward the article in the carrier. The first convey segment and the second convey segments are also spaced apart from one another in the convey direction.

In yet another aspect of the present disclosure, a heating system for heating articles is provided. The heating system includes a preheating section for heating an article, a cooling section for cooling the article, and a heating section for heating the article using microwave energy. The heating section is disposed between the preheating section and the cooling section and include multiple heating chamber modules. Each of the heating chamber modules includes a vessel segment having an inlet and an outlet, at least one microwave launcher configured to discharge microwave energy into the vessel segment, a convey segment disposed within the vessel segment for transporting the article in a convey direction, and a conveyor driver for driving the convey segment. The chamber modules are configured to be selectively coupled to and uncoupled from one another.

In another aspect of the present disclosure, a process for heating articles in a heating system is provided. The process includes passing a carrier loaded with an article through a vessel inlet and into a first vessel portion. The loaded carrier is moved in a first direction through the first vessel portion away from the inlet. During at least a portion of the moving in the first direction, at least a portion of the articles in the loaded carrier is contacted with a first fluid medium. The process further includes moving the loaded carrier in a second direction opposite the first direction through a second vessel portion toward a vessel outlet and, during at least a portion of the moving through the second vessel portion, contacting at least a portion of the articles in the loaded carrier with a second fluid medium.

In yet another aspect of the present disclosure, a heating system is provided that includes a heating chamber configured to heat articles using microwave energy. The heating chamber includes a chamber adapted to be at least partially filled with a fluid medium, a conveyor for transporting carriers holding the articles through the heating chamber in a convey direction, and a vessel. The vessel includes an inlet side and an outlet side with the inlet side and the outlet side being at least partially fluidly isolated from one another. The vessel further includes a carrier inlet configured to receive one of said carriers into said inlet side, a carrier outlet configured to discharge one of said carriers out of said outlet side, a first convey segment located in the inlet side configured to move the carriers vertically away from the carrier inlet; and a second convey segment located in the outlet side configured to move the carriers vertically toward the carrier outlet.

In still another aspect of the present disclosure, a process for heating articles is provided. The process includes preheating an article in a carrier in a preheat section and, after the preheating, heating the article in the carrier in a heating section, wherein at least a portion of the heating is performed using microwave energy. The process further includes passing the article in the carrier through a holding section, wherein a coldest temperature of the article is maintained at or above a hold temperature for a hold time and cooling the article in the carrier in a cooling section. At least a portion of one or more of the preheating, the passing, and the cooling are performed by moving the carrier at least one of upwardly and downwardly using at least one convey segment, and the article is contacted by at least one fluid medium during movement.

BRIEF DESCRIPTION OF THE DRAWINGS

The foregoing and other objects, features, and advantages of the present disclosure set forth herein will be apparent from the following description of particular embodiments of those inventive concepts as illustrated in the accompanying drawings. It should be noted that the drawings are not necessarily to scale; however, emphasis instead is being placed on illustrating the principles of the inventive concepts. It is intended that the embodiments and figures disclosed herein are to be considered illustrative rather than limiting.

DETAILED DESCRIPTION

Figure 1A:
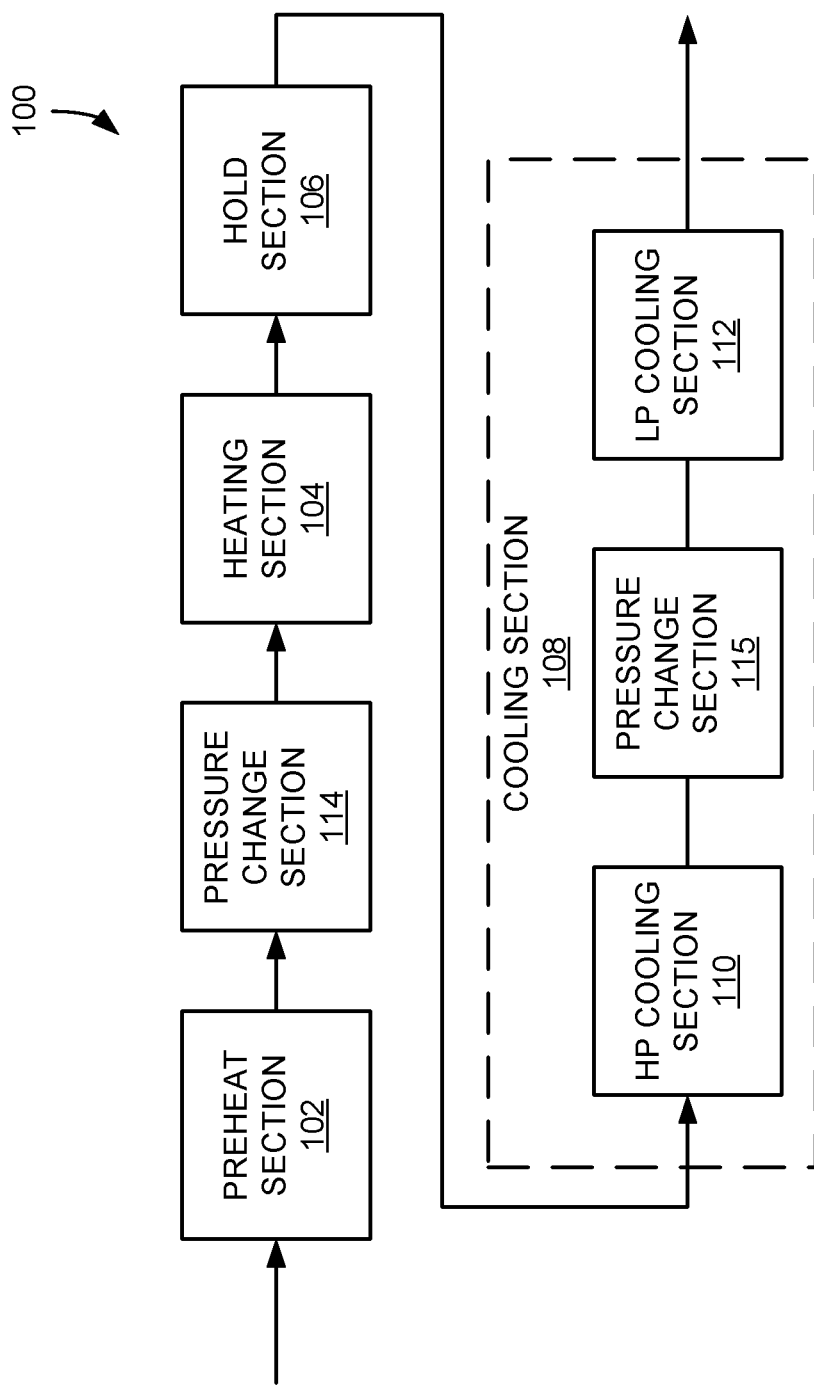
FIG. 1A is a block diagram illustrating an example heating system in accordance with the present disclosure.

The present disclosure relates to methods and systems for heating articles using an efficient, commercial-scale microwave heating system. The processes and systems described herein are particularly useful for heating systems configured for the pasteurization and/or sterilization of articles including, for example, packaged foodstuffs and other items.

In general, pasteurization involves the rapid heating of an item to a minimum temperature between about 80° C. and about 100° C., while sterilization involves heating an item to a minimum temperature between about 100° C. and about 140° C. In some cases, pasteurization and sterilization may take place simultaneously, or nearly simultaneously and, consequently, articles being sterilized are generally also pasteurized due to the temperature required for sterilization being greater than that for pasteurization. Examples of items that may be pasteurized and/or sterilized include, but are not limited to, packaged foodstuffs, medical instruments and fluids, dental instruments and fluids, veterinary fluids, and pharmaceutical fluids. Foodstuffs can include, but are not limited to, fruits, vegetables, meats, pastas, pre-made meals, soups, stews, jams, and beverages.

The items being pasteurized or sterilized may be packaged. The packages may be formed of any suitable material including, but not limited to, various types of plastic, cellulosic materials, and any other at least partially microwave-transparent materials. Specific types of packages include, but are not limited to, bottles, trays, cartons, bags, pouches, spouted pouches, tubes, and tubs.

Packages for use in containing items during processing (including heating) may have any suitable size and shape. For example, each package can have a length of at least about 1 inch, at least about 2 inches, at least about 4 inches, or at least about 6 inches and/or not more than about 18 inches, not more than about 12 inches, not more than about 10 inches, not more than about 8 inches, or not more than about 6 inches, and each package may have a width of at least about 1 inch, at least about 2 inches, at least about 4 inches, at least about 4.5 inches, or at least 5 inches and/or not more than about 12 inches, not more than about 10 inches, not more than about 8 inches, or not more than 6 inches. In certain applications, the width of the package may be limited by several physical constraints including, without limitation, structural limitations of the equipment used to process the package. Width may also be restricted based on the placement and orientation of the microwave launchers used to deliver microwave energy to the package. For example, a microwave launcher may have a certain displacement relative to the package during processing and the microwave beam provided by the launcher may have a maximum width at that displacement. As a result, to ensure that the package receives relatively uniform exposure to the microwave beam, the width of the package may be limited to the maximum width of the microwave beam at the displacement.

Additionally, the depth/thickness of each package may be at least about 0.5 inches, at least about 1 inch, or at least about 1.5 inches and/or not more than about 8 inches, not more than about 6 inches, or not more than about 3 inches. As with the width of the package, the depth/thickness of the package may be dictated by limitations of the heating system. For example, the thickness of the package may be dictated or otherwise limited by the degree of penetration achievable with the microwave energy provided by the heating system for the particular package being heated.

As used herein, the terms "length" and "width" refer to the longest and second longest, respectively, non-diagonal dimensions of the package. When the package has a trapezoidal shape such that the top of the package is longer and wider than its bottom, the length and width are measured at the largest cross-section (usually the top surface). The height is the shortest non-diagonal dimension measured perpendicular to the plane defined by the length and width. In addition to rectangular or trapezoidal shapes, packages contemplated herein further include those including at least one rounded surface. Such packages may be, for example, spherical, ovoid, or cylindrical, the latter of which may include one of a circular, elliptical, or irregularly rounded profile.

In one specific example, the microwave energy may be discharged or otherwise directed into various locations discussed herein by one or more launchers. As used herein, the term "microwave energy" generally refers to electromagnetic energy having a frequency between about 300 MHz and about 30 GHz. Microwave energy of varying frequencies can be used, but energy having a frequency of about 915 MHz or about 2.45 GHz (2450 MHz) may be preferred. In some cases, the electromagnetic energy used to heat articles may be polarized. In addition to microwave energy, one or more other types of heat sources may also be used, at least in part, to heat articles in systems and methods according to the present disclosure. Such additional types of heat may include, for example, various conductive or convective heating methods or devices. However, it is generally preferred that at least about 50, at least about 55, at least about 60, at least about 65, at least about 70, at least about 75, at least about 80, at least about 85, at least about 90, or at least about 95 percent of the energy used to heat articles during the pasteurization or sterilization heating step be microwave energy.

Figure 1B:
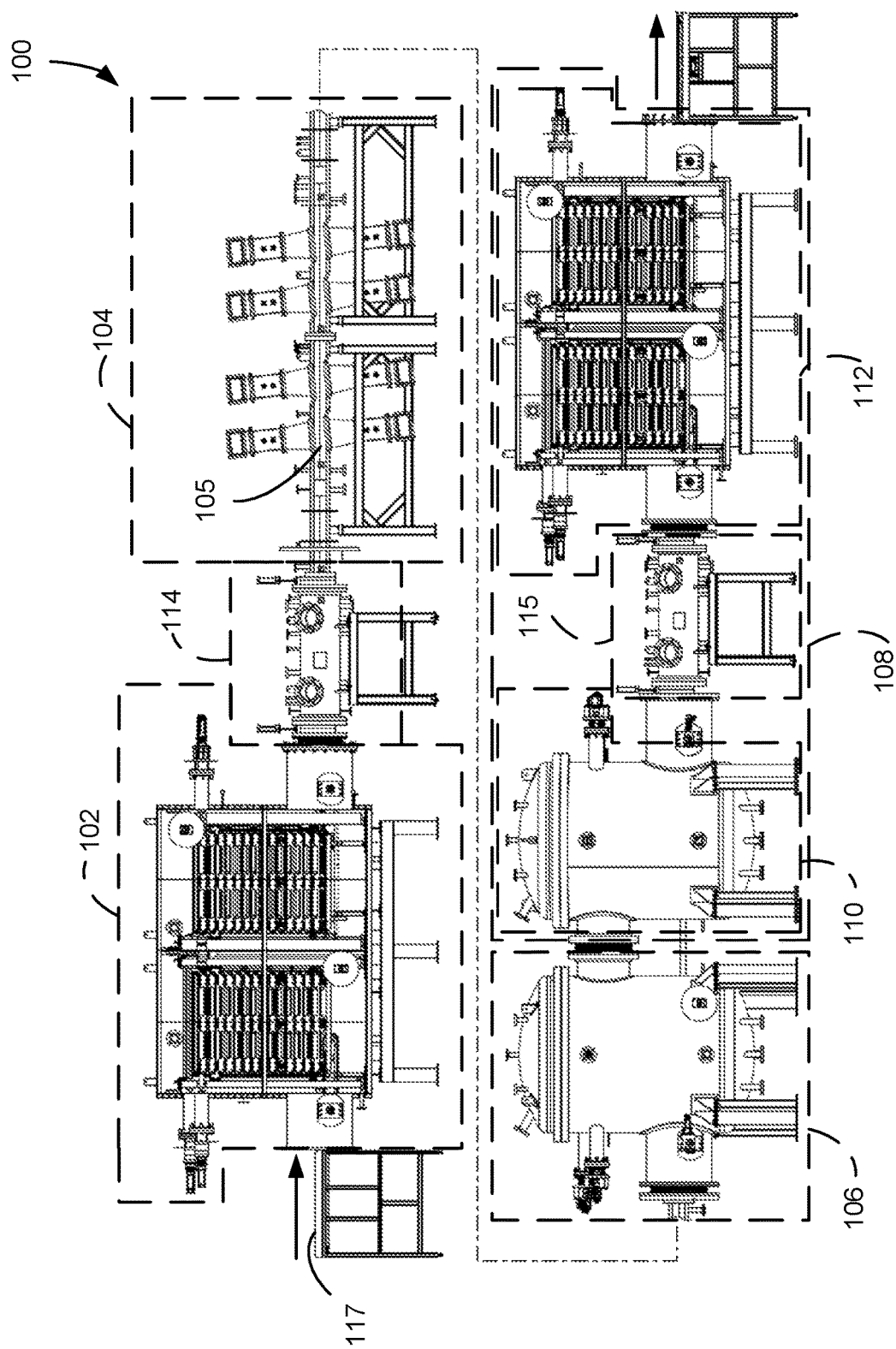
FIG. 1B is a schematic illustration of the heating system of FIG. 1A.

Turning now to FIGS. 1A and 1B, below, schematic diagrams of the main steps of a heating process and the main elements of a heating system 100 suitable for pasteurizing or sterilizing articles according to aspects of the present disclosure are provided. As shown in FIGS. 1A and 1B, the heating system 100 may include a preheat section 102, a heating section 104, a hold section 106, a cooling section 108, and pressure change sections 114, 115. Articles, which may be packaged and loaded into carriers (such as the carrier 10 shown in FIGS. 2A-2C) may be introduced into the preheat section 102. In the preheat section 102, the articles are heated to have a substantially uniform temperature throughout. By doing so, the articles are made to be in a predictable initial state prior to being passed through subsequent sections of the heating system 100.

Once preheated, the articles may be passed through the pressure change section 114 before being introduced into the heating section 104. The pressure change section 114 functions as an air/pressure lock between the preheat section 102, which may be at atmospheric pressure, and the heating section 104, which may be pressurized relative to the preheat section 102. Among other reasons, such pressurization may be implemented to prevent packaging of the article from expanding or rupturing as the article is heated.

In the heating section 104, the articles may be rapidly heated using microwave energy discharged into the heating section 104 by one or more launchers. The heated articles may then be passed into the hold section 106, wherein the articles are permitted to thermally equilibrate such that the coldest portion of each article is maintained at a temperature at or above a target temperature (e.g., a pasteurization or sterilization target temperature) for a specified amount of time.

Subsequently, the articles may be passed to the cooling section 108, where the articles may be cooled to a suitable handling temperature. In some cases, as shown in FIGS. 1A and 1B, the cooling section 108 may be divided into a high-pressure cooling section 110 and a low-pressure cooling section 112, and can include another pressure change section 115 between the two cooling sections 110, 112. Alternatively, the cooling section 108 may include a single cooling section with a pressure change section located upstream or downstream of the cooling section 108. As used herein, the term "upstream" and "downstream" refer to the relative positions of various components, zones, sections, etc. along the main flow path through the heating system 100. A component, zone, or section located prior to another can be said to be "upstream" of that component, while a component, zone, or section located after another may be said to be "downstream" of that component.

In some cases, two or more of the preheat section 102, the microwave heating section 104, the hold section 106, and the cooling sections 108-112 may be defined within a single vessel, while, in other cases, at least one of these sections may be defined within one or more separate vessels. Additionally, in some cases, one or more of the vessels may be configured to be at least partially filled with a fluid medium such that a liquid bath is formed in which the articles being processed may be at least partially submerged during processing. As used herein, the term "at least partially filled" means at least 25 percent of the volume of the specified vessel is filled with a fluid medium. In some cases, the volume of at least one of the vessels used in the preheat section, the microwave heating section, the hold section, and the cooling section can be at least about 50 percent, at least about 75 percent, at least about 90 percent, at least about 95 percent, nearly 100 percent, or completely filled with a fluid medium.

When present, the fluid medium used may include any suitable type of fluid. In some cases, the fluid medium may have a dielectric constant greater than the dielectric constant of air and/or a dielectric constant similar to the dielectric constant of the articles being processed. Water (or a fluid medium including water) may be particularly suitable for systems used to heat consumable articles. The fluid medium may also include one or more additives, such as, for example, oils, alcohols, glycols, and salts, to alter or enhance physical properties of the fluid medium (e.g., boiling point) at the operating conditions of the system.

As used herein and unless otherwise specified, the term "fluid" or "fluid medium" is intended to encompass both liquids, such as those described above in the context of liquid baths within which articles may be at least partially submerged, and gases. For example and without limitation, such gases may include air, inert gases such as nitrogen, or any other suitable gas for use in the various applications described herein. As previously noted, vessels, chambers, and other volumes discussed herein that are at least partially filled with a fluid in a liquid form are referred to as containing a "liquid bath". Unless so identified, it should be assumed that such volumes may be partially filled with either a liquid or gaseous fluid.

The microwave heating system 100 may include a convey system 117 (shown in FIG. 1B) including one or more conveyor segments for transporting the articles through one or more of the processing sections described above. Examples of suitable types of conveyor segments include, but are not limited to, plastic or rubber belt conveyors, chain conveyors, roller conveyors, flexible or multi-flexing conveyors, wire mesh conveyors, bucket conveyors, pneumatic conveyors, screw conveyors, trough or vibrating conveyors, and combinations thereof. Any suitable number of individual convey segments can be used with the conveyance system, and the convey segment or segments may be arranged in any suitable manner within the vessels and other sections of the heating system 100. Other examples of convey systems suitable for use in implementations of the present disclosure are described in U.S. Pat. No. 9,357,590, entitled "Microwave Heating System with Enhanced Temperature Control" ("the '590 Patent"), the entirety of which is incorporated herein by reference.

Figure 2A:
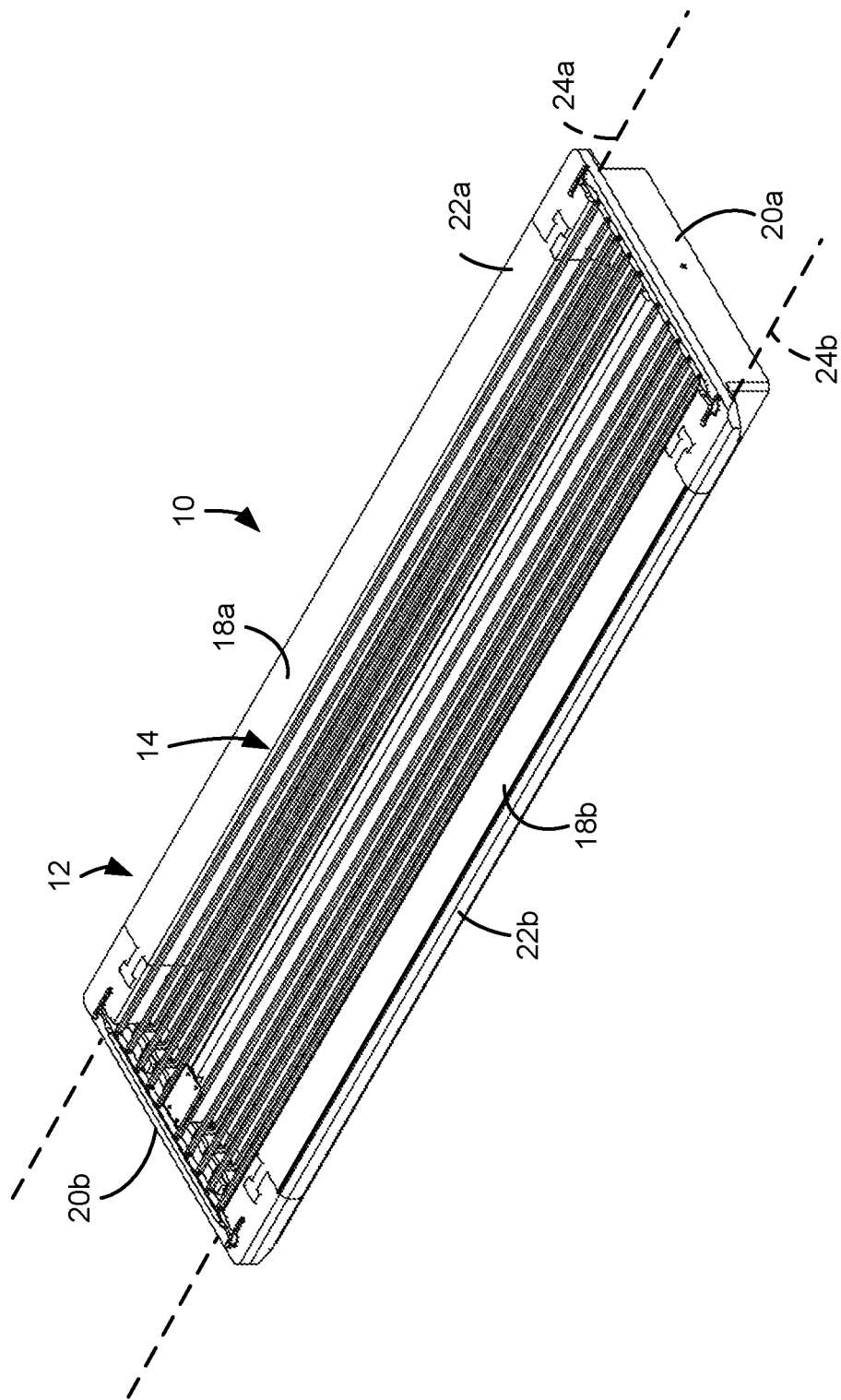
FIG. 2A is an isometric view of an example carrier that may be used in heating systems according to the present disclosure, such as the heating system of FIGS. 1A and 1B
Figure 2B:
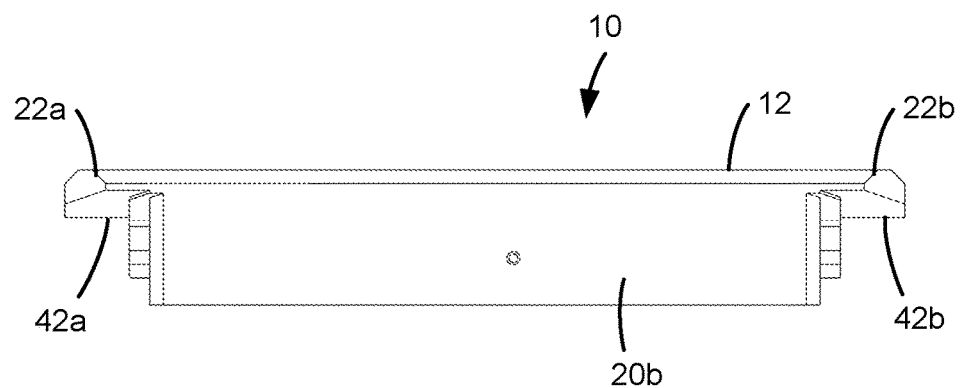
FIG. 2B is an elevation view of an end of the carrier of FIG. 2A.
Figure 2C:
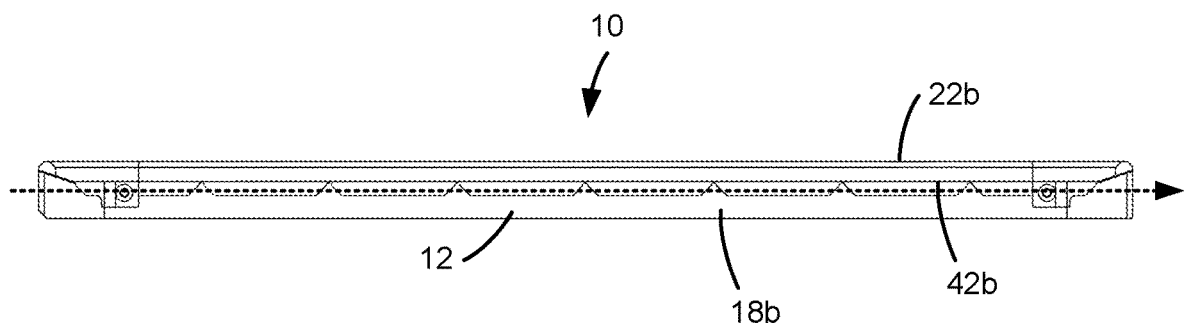
FIG. 2C is an elevation view along a side of the carrier of FIG. 2A.

Articles heated in heating systems as described herein may be secured in a carrier configured to transport the articles through the system. Several views (isometric, front, and side) of an exemplary carrier 10 are provided in FIGS. 2A-2C. As generally shown in FIGS. 2A-2C, the carrier 10 may include an outer frame 12, and an upper support structure 14. The outer frame 12 may include two spaced-apart side members 18a, 18b and two spaced-apart end members 20a, 20b. The first and second end members 20a, 20b may be coupled to and extend between opposite ends of first and second side members 18a, 18b to form the outer frame 12. When side members 18a, 18 are longer than the end members 20a-b, the frame may have a generally rectangular shape, as shown in FIG. 2A.

Although FIGS. 2A-2C describe the example carrier 10 as having a substantially rectangular shape, carriers having other shapes may also be used in implementations of heating systems according to this disclosure. More generally, carriers for use in heating systems of the present disclosure may have any suitable shape provided they are able to support one or more articles for heating and are conveyable through the heating system by a corresponding conveyor system.

As shown in FIGS. 2A-2C, the first and second side members 18a, 18b of the carrier each include respective support projections 22a, 22b that are configured to engage respective first and second convey line support members, which are represented by dashed lines 24a, 24b in FIGS. 2A and 2C. The first and second support projections 22a, 22b of the carrier 10 further include first and second lower support surfaces 42a, 42b for supporting the carrier 10 on the first and second convey line support members 24a, 24b. Convey line support members 24a, 24b may be moving convey line elements such as, for example, chains, belts, or similar mechanisms located on each side of the carrier 10 as it moves through the heating system in a direction represented by the arrow 50 in FIG. 2C.

Carriers suitable for use in the heating system described herein may be formed of any suitable materials, including low loss materials, and, in some cases, even electrically conductive materials. Additional details regarding other suitable carriers are provided in U.S. patent application Ser. No. 15/284,173 ("the '173 Application"), the entirety of which is incorporated herein by reference.

When loaded into a carrier, the articles may be arranged in rows extending along the length or width of the carrier. Depending on the size, shape, and/or type of package, the individual articles may be arranged in certain configurations such as, for example, a nested configuration as described in the '704 Application. In some cases, dividers or other support devices may be used in addition to the upper and lower support structures of the carrier to hold the articles in place during processing.

As generally shown in FIGS. 1A and 1B, loaded carriers may be initially introduced into the preheat section 102, wherein the articles may be heated and/or thermally equilibrated to achieve a substantially uniform temperature. Among other benefits, preheating articles such that they are at a substantially uniform temperature improves reliability of the heating process by reducing the thermal variability within an article and across multiple articles being processed using the heating system 100. In other words, the preheat section 102 may be used to ensure that articles leaving the preheat section 102 are in the same or approximately the same thermal state to facilitate predictable and repeatable results for subsequent heating processes, such as the microwave-based heating that subsequently occurs in the heating section 104. In some cases, at least about 75 percent, at least about 80 percent, at least about 85 percent, at least about 90 percent, at least about 95 percent, at least about 97 percent, or at least about 99 percent of all the articles exiting the preheat section 102 have a minimum temperature within about 10° C., within about 8° C., within about 5° C., within about 2° C., or within about 1° C. of one another. This preheating step may also be called "thermalization" or "thermalizing," which generally refers to temperature equilibration or equalization. In some cases, the temperature of the coldest portion of the articles introduced into the preheat section 102 may be not more than about 45° C., not more than about 40° C., not more than about 35° C., not more than about 30° C., not more than about 27° C., or not more than about 25° C.

When the preheat section 102 is at least partially filled with a fluid medium to form a liquid bath, the articles can be at least partially submerged in the liquid bath as the carrier passes through the preheat section 102. The fluid medium of the liquid bath in the preheat section 102 can be warmer than the temperature of the articles passing therethrough. In some cases, the liquid bath may have an average bulk temperature of at least about 25° C., at least about 30° C., at least about 35° C., at least about 40° C., at least about 45° C., at least about 50° C., at least about 55° C., or at least about 60° C. and/or not more than about 100° C., not more than about 95° C., not more than about 90° C., not more than about 85° C., not more than about 80° C., not more than about 75° C., not more than about 70° C., not more than about 65° C., or not more than about 60° C. This may be at least about 2° C., at least about 5° C., at least about 10° C., at least about 15° C., or at least about 20° C. and/or not more than about 35° C., not more than about 30° C., not more than about 25° C., or not more than about 20° C. warmer than the temperature of the coldest portion of the articles being transported through the preheat section 102.

The preheating step can be carried at ambient pressure or it may be carried out under pressure. When pressurized, the preheating step may be performed at a pressure of at least about 5 psig, or at least about 10 psig and/or not more than about 80 psig, not more than about 50 psig, not more than about 40 psig, or not more than about 25 psig. In some cases, the preheating step may be performed at or near atmospheric pressure of less than about 5 psig, not more than about 3 psig, not more than about 2 psig, or not more than about 1 psig. When the preheat section 102 is pressurized and at least partially filed with a fluid the pressure values are understood to be in addition to any head pressure exerted by the fluid. The residence time for articles passing through the preheat section 102 may vary for different applications. For example, in certain applications, the articles may have an average residence time of at least about 1 minute, at least about 5 minutes, or at least about 10 minutes and/or not more than about 60 minutes, not more than about 20 minutes, or not more than about 10 minutes. By controlling residence time and temperature within the preheat section 102, articles exiting from the preheat section 102 can be made to have various average temperatures as required for particular applications. For example, and without limitation, articles exiting the preheat section 102 may have an average temperature of at least about 20° C., at least about 25° C., at least about 30° C., or at least about 35° C. and/or not more than about 90° C., not more than about 75° C., not more than about 60° C., or not more than about 50° C.

Figure 3A:
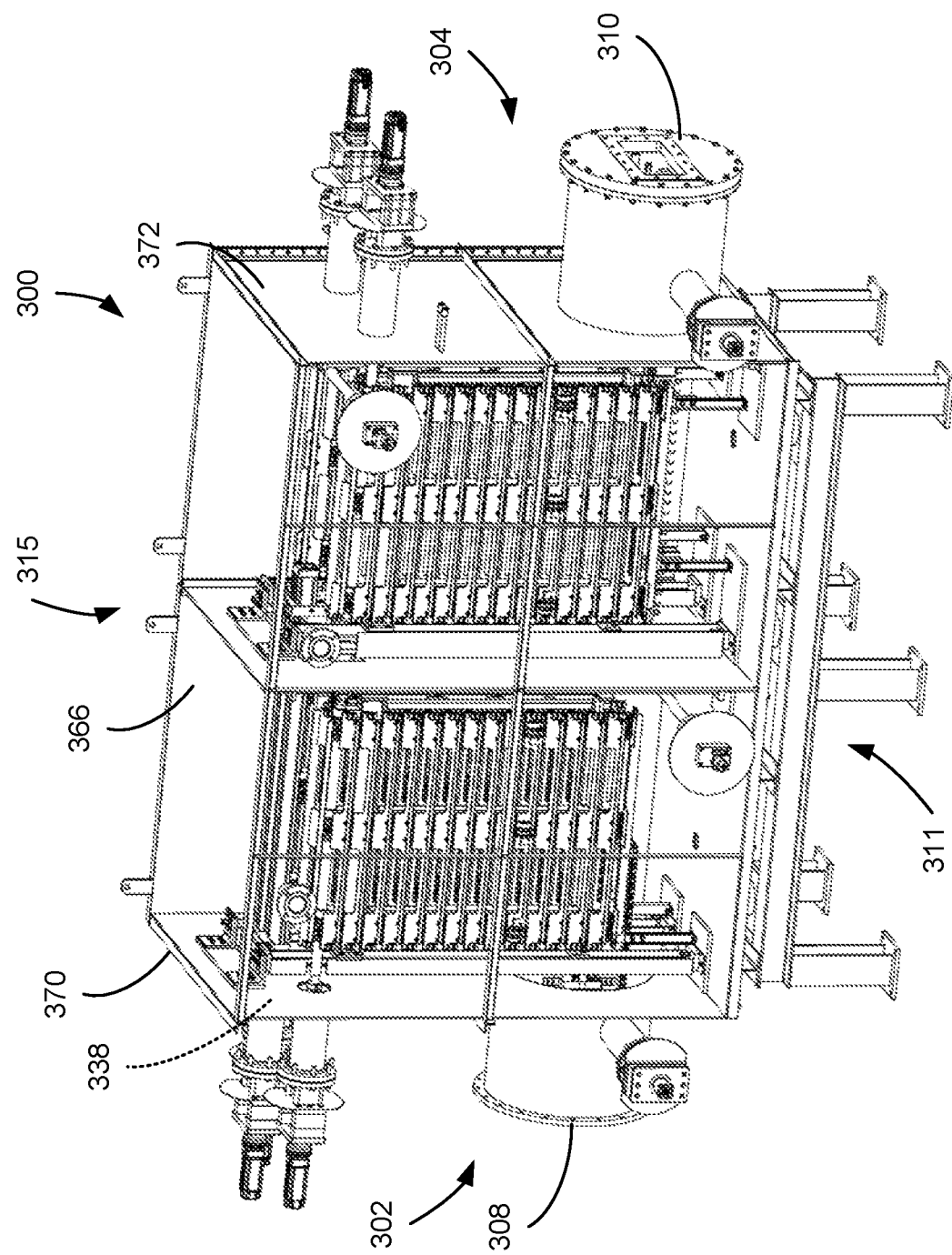
FIG. 3A is an isometric view of a vessel that may be included for various purposes in heating systems according to the present disclosure.
Figure 3B:
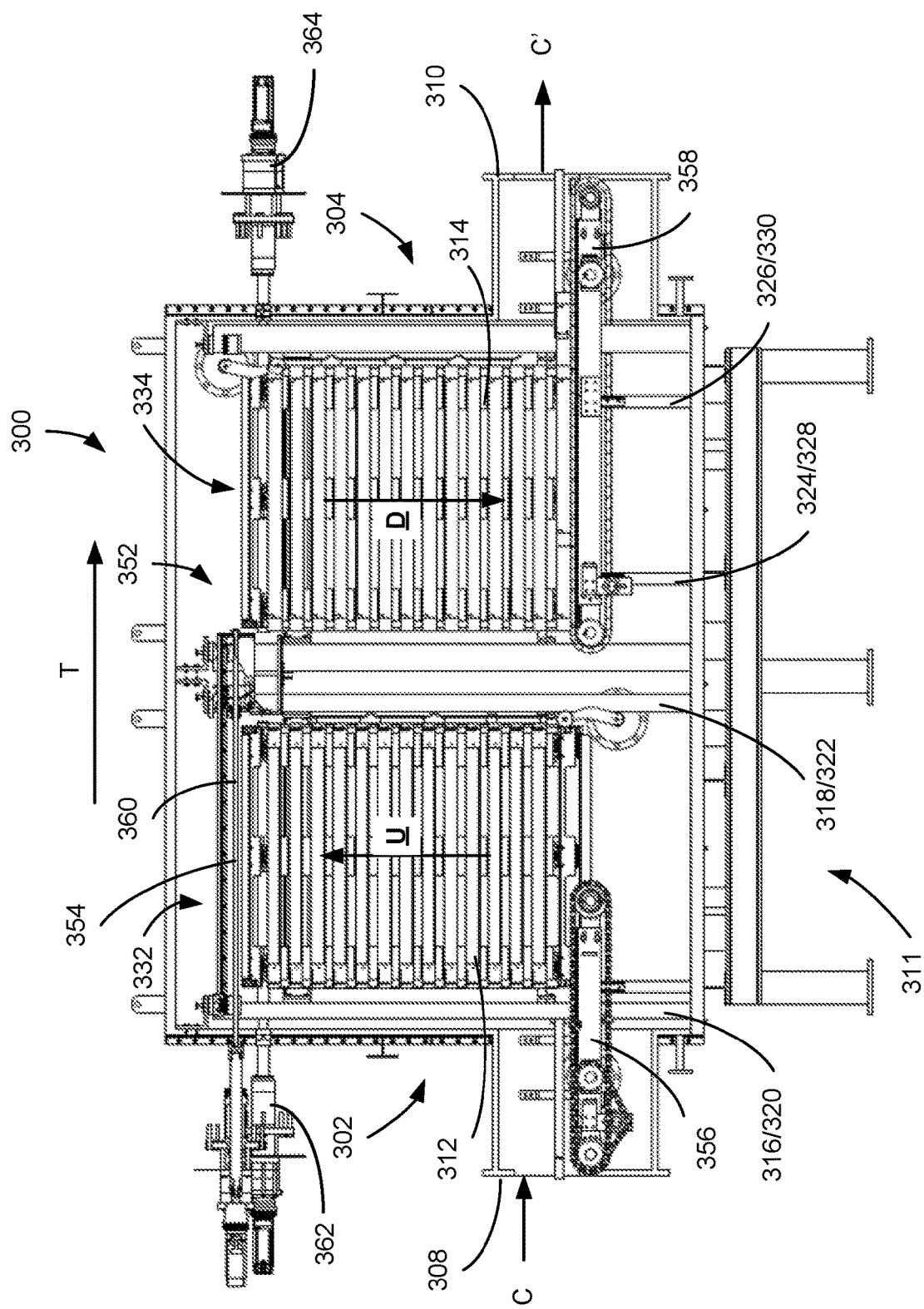
FIG. 3B is a cross-sectional view along a side of the vessel of FIG. 3A.
Figure 3C:
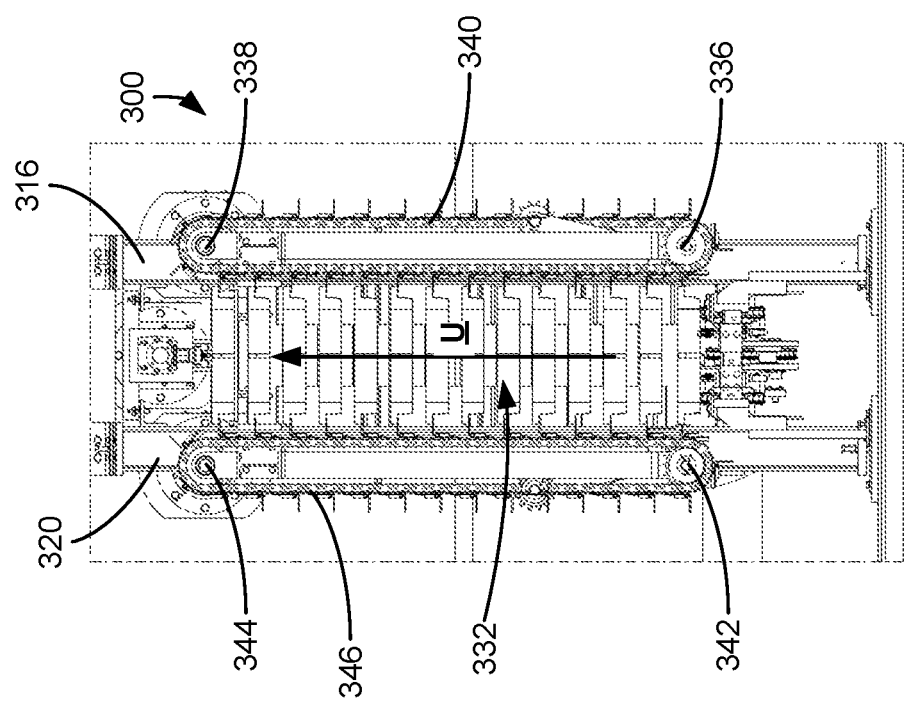
FIG. 3C is a cross-sectional view from an end of the vessel of FIG. 3A.

Turning now to FIGS. 3A-3C, several views of an exemplary preheat vessel 300 suitable for use in the preheat section 102 are provided. As shown in FIGS. 3A-3B, the preheat vessel 300 can be a vessel that has an inlet side 302 and an outlet side 304, which are at least partially fluidly isolated from one another. The inlet side 302 and the outlet side 304 may be defined in a single vessel shell 306, as illustrated, or the inlet side 302 and the outlet side 304 may be defined in separate vessel shells (not shown) that may also be at least partially thermally isolated from one another.

The vessel 300 shown in FIGS. 3A and 3B further includes a carrier inlet 308 for receiving loaded carriers into the inlet side 302 of the vessel 300 and a carrier outlet 310 for discharging loaded carriers from the outlet side 304 of the vessel 300. In certain implementations, such as that illustrated in FIGS. 3A-3C, both the carrier inlet 308 and the carrier outlet 310 are positioned near a lower vertical end 311 of the vessel 300 such that the carriers are introduced into and/or withdrawn from the lower one-half, or the lower one-third, of the interior volume of the inlet side 302 and/or the outlet side 304 of the vessel 300, respectively. Both the carrier inlet 308 and the carrier outlet 310 may be configured such that only single-stacked carriers may pass through the carrier inlet 308 and the carrier outlet 310. Although the overall heating system and preheat section may be configured to facilitate the continuous or near-continuous passage of carriers therethrough, the carrier inlet 308 and the carrier outlet 310 may be configured such that only one carrier passes through them at a time.

In certain implementations, one or both of the carrier inlet side 302 and the carrier outlet side 304 may be at least partially filled with a fluid medium to form respective liquid baths. In such implementations and to the extent the carrier inlet 308 and/or the carrier outlet 310 are located below the level of the liquid baths, the carrier inlet 308 and/or the carrier outlet 310 may include a water lock (or similar fluid isolation system) configured to permit passing of carriers into or out of the vessel 300 without loss or fluid medium from within the vessel 300. In certain implementations, the carrier inlet 308 and/or the carrier outlet 310 may also be disposed between sections of heating systems having different operating pressures. In such instances, the carrier inlet 308 and/or the carrier outlet 310 may incorporate a pressure lock (or similar pressure isolation system) for passing carriers into and/or out of the vessel 300 without substantial pressure loss from within the vessel 300 (if pressurized) or adjacent equipment.

Referring now to FIGS. 3B-3C, carriers are transported through the vessel 300 using multiple conveyor segments. For example, carriers are first received by an inlet conveyor segment 356 extending through the carrier inlet 308. As illustrated in FIG. 3B, the inlet conveyor segment 356 may generally transport carriers in an inlet direction C. Each of the inlet side 302 and the outlet side 304 of the vessel 300 may further include a respective conveyor segment 312, 313 for moving carriers through the vessel 300. Each conveyor segment 312, 313 may be, for example, a vertical conveyor segment configured to transport the carriers in a direction generally perpendicular to the direction of carrier travel. For example, as shown in FIG. 3B, the first conveyor segment 312 located in the inlet side 302 of the vessel 300 is configured to move carriers upwardly away from the carrier inlet 308, as shown by arrow U in FIG. 3B, while the second conveyor segment 313 located in the outlet side 304 of the vessel 300 is configured to move carriers downwardly toward the carrier outlet 310, as shown by arrow D. Additional conveyor segments, which may be aligned with the direction of carrier travel, may be located in or near the carrier inlet 308 and/or the carrier outlet 310 to facilitate movement of the carriers into and out of the vessel 300. After being transported by the second conveyor segment 313, carriers may be placed onto an outlet conveyor segment 358 that transports the carriers in an outlet direction C'. As shown in the implementation of FIG. 3B, the outlet direction C' may be in line with the inlet direction C, although in other implementations, C' may be in a different direction relative to the inlet direction C.

FIG. 3C is a vertical section through the inlet side 302 of the vessel 300 and is representative of the internal components of each of the inlet side 302 and the outlet side 304 of the vessel 300. As shown in FIGS. 3B-3C, each vertical conveyor segment 312, 314 includes a respective set of vertical support members. For example, the vertical conveyor segment 312 includes vertical support members 316-322 (vertical support members 320 and 322 are hidden behind vertical support members 316 and 318, respectively in FIG. 3B; vertical support member 320 is shown in FIG. 3C) while the vertical conveyor segment 314 includes vertical support members 324-330 (with the vertical support members 328 and 330 hidden behind vertical support members 324 and 326, respectively, in FIG. 3B). The vertical support members 316-322 of the vertical conveyor segment 312 are spaced apart from one another such that the vertical support members 316-322 define a first carrier receiving space 332 therebetween. Similarly, the vertical support member 324-330 of the vertical conveyor segment 314 are spaced apart from one another such that the vertical support members 324-330 define a second carrier receiving space 334 therebetween. As a result of such spacing, the carriers may be conveyed into and out of the vessel 300, as shown by arrows C in FIG. 3B.

Each vertical support member includes a pair of opposite gears and a flexible support member in contact with and movable by the gears. For example, as illustrated in FIG. 3C, the vertical support member 316 includes gears 336, 338 and flexible support member 340 while the vertical support member 320 includes gears 342, 344 and flexible support member 346, where each of the flexible support members 340 and 346 are illustrated as belts. Other examples of suitable flexible support members may include, but are not limited to, cables and chains. As shown, for example, in FIG. 3C, each of the flexible support members 340, 346 further includes a plurality of carrier support members, which are configured to contact support projections of the carriers, such as the support projections 22a, 22b of the carrier 10 illustrated in FIGS. 2A-B), and which are discussed below in more detail in the context of FIG. 3D.

Figure 3D:
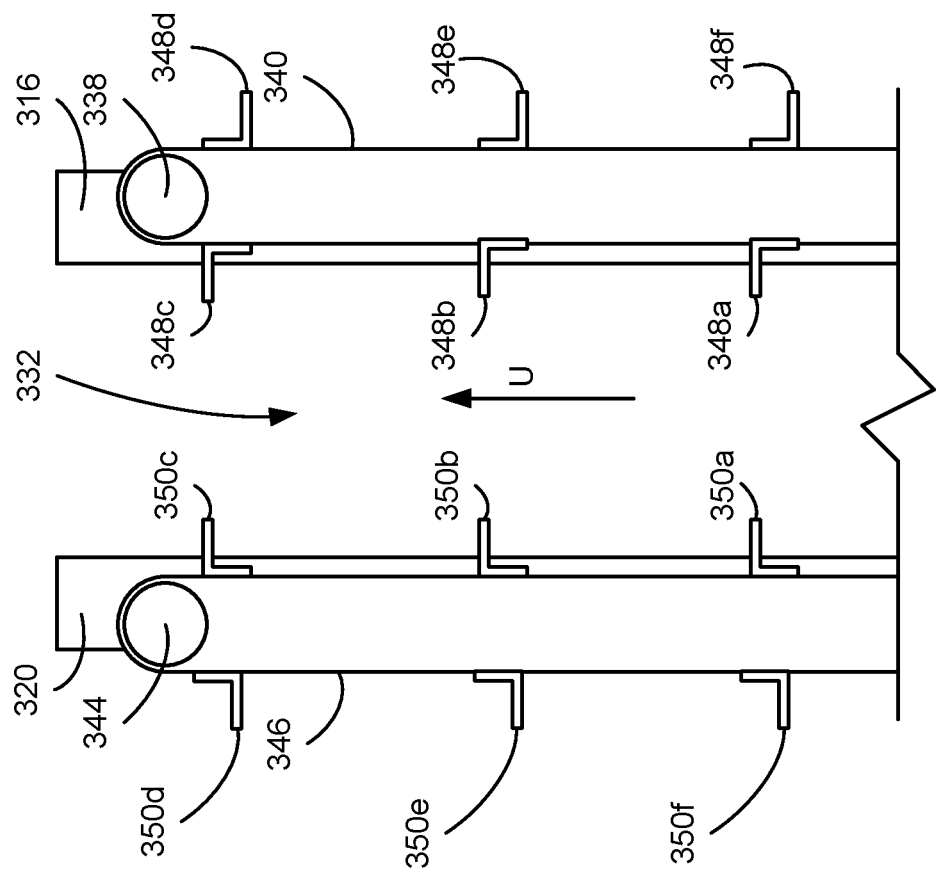
FIG. 3D is a schematic illustration of support members of the vessel of FIG. 3A used to convey carriers, such as the carrier of FIGS. 3A-3C.

FIG. 3D is a schematic partial view of the flexible support members 340, 346 and is illustrative of other flexible support members included in implementations of the present disclosure. As show in FIG. 3D, each flexible support member 340, 346 includes a respective set of carrier support members coupled thereto. More specifically, flexible support member 340 includes carrier support members 348a-f and flexible support member 344 includes carrier support members 350a-f. The carrier support members 348a-f, 350a-f may be arranged in an engaged configuration when the carrier support members 348a-f, 350a-f are located within the carrier receiving space 332 and in a disengaged configuration when the carrier support members 348a-f, 350a-f are located outside the carrier receiving spaces 332. For example, as illustrated in FIG. 3D, carrier support member 348a-c and 350a-c are in an engaged configuration wherein they can receive and transport a carrier while carrier support members 348d-f and 350d-f are in a disengaged configuration. The carrier support members 348a-f, 350a-f may be transitioned between the engaged and the disengaged configurations by moving the corresponding flexible support member 340, 346, such as by driving the gears 336, 338 (for flexible support member 340) and gears 342, 344 (for flexible support member 346). When the carrier support members 348a-f, 350a-f are arranged in an engaged configuration within the carrier receiving space 332 corresponding carrier support members of the flexible support members 340, 346 form a pair of carrier support members (e.g., carrier support members 348a and 350a) that are configured to contact the lower support surfaces of the carriers.

Referring now to FIG. 3B, as gears 336, 338 and gears 342, 344 rotate, the flexible support members 340, 346 move which causes a given pair of carrier support structures engaged to a corresponding carrier to move the carrier upwardly (i.e., in the U direction). Once the carrier reaches the top of the carrier receiving space 332, another conveyor segment may remove the carrier from the carrier receiving space 332. In the example shown in FIG. 3B, a transfer section 352 including a conveyor segment 354 that may remove carriers from the top of the vertical conveyor segment 312 located on the inlet side 302. After the carrier is removed from the vertical conveyor segment 312, the carrier support members (such as the carrier support members 348a-f, 350a-f indicated in FIG. 3D) transition from an engaged configuration to a disengaged configuration as they travel to the bottom of the vertical support members 316-322 on the flexible support member 340. Once at the bottom of the vertical support members 316-322, the carrier support members 348a-f, 350a-f transition back to an engaged configuration and receive another carrier for transporting upwardly within the carrier receiving space 332.

Meanwhile, the carrier is transferred through the transfer segment 352 to the vertical conveyor segment 314 disposed on the outlet side 304 of the vessel 300. The vertical conveyor segment 314 is substantially similar to the vertical conveyor segment 312 except for that flexible support members of the vertical conveyor segment 314 are driven opposite those of the vertical conveyor segment 312. As a result, after a carrier is received within the vertical conveyor segment 314, the carrier is transferred downwardly (i.e., in the D direction) until it reaches an outlet conveyor segment 358. The outlet conveyor segment 358 receives the carrier and then directs the carrier out of the carrier outlet 310 (i.e. in the C' direction).

The transfer section 352 is configured to permit the transfer of a carrier from the inlet side 302 to the outlet side 304, as shown by arrow T in FIG. 3B. In certain implementations, the transfer section 352 may be in the upper one-half, or upper one-third, of the interior volume of the vessel 300 and may be at least partially fluidly and/or thermally isolated from each of the inlet side 302 and/or outlet side 304. For example, in certain implementations, the transfer section 352 may be fluidly isolated from each of the inlet side 302 and/or the outlet side 304 by being disposed above a liquid bath or spray nozzles that may be disposed in the inlet side 302 or the outlet side 304. In other implementations, a weir structure or similar barrier may be implemented between the transfer section 352 and inlet side 302 and/or outlet side 304 to prevent overflow into or out of the transfer section 352. Such a structure may be formed, in part, from a material having low thermal conductivity to reduce heat transfer between sections. As shown in FIG. 3B, the transfer section 352 may be configured such that only single-stacked carriers may pass through the transfer section 352. Thus, only individual carriers, not groups of two or more carriers stacked upon one another, may be permitted to move from the inlet side 302 to the outlet side 304 of the vessel 300 via the transfer section 352.

As generally shown in FIGS. 3A and 3B, the transfer section 352 may include a conveyor segment 354 for moving the carrier from the inlet side 302 of the vessel 300 to the outlet side 304 of the vessel 300. The conveyor segment 354 can have any suitable configuration and, in some cases, may be a horizontal conveyor segment for moving the carrier in a direction generally parallel to the direction of carrier travel. In operation, when a carrier reaches the top of the vertical conveyor segment 312, a pusher arm 360, tab, or other such device of the first vertical conveyor segment 312 may contact the carrier and push it from the top of the vertical conveyor segment 312 to the top of the vertical conveyor segment 314 of the outlet side 304. As the carrier enters the carrier receiving space 334 of the vertical conveyor segment 314, its lower contact supports contact a pair of carrier receiving members, which transition into an engaged configuration and hold the carrier as it is transported downwardly (i.e. in the direction D) toward the carrier outlet 310. The pusher arm 360 then retracts until another carrier is ready to be transferred.

Each of the vertical conveyor segments 312, 314 may include a driver 362, 364 for controlling rotation of the respective gears. Additionally, the horizontal conveyor segment 354 may include a driver (not shown) for moving the pusher arm 360 back and forth within the vessel 300. In some cases, at least a portion of one or more of the drivers may be disposed outside the internal volume of the vessel 300, as generally shown with drivers 362 and 364 in FIG. 3B. The drivers of each of the conveyor segments may be individually controllable so that each conveyor segment is movable independent of the others. However, the individual movements of each conveyor segment may be coordinated so that carriers move through the vessel 300 in a generally continuous manner.

In operation, a first carrier passes through the carrier inlet 308, such as by being transported by the inlet conveyor segment 356, and into the carrier receiving space 332 of the first conveyor segment 312 located on the inlet side 302. As the carrier enters the carrier receiving space 332, its lower support surface contacts a pair of carrier support members arranged in an engaged configuration, which support the carrier. The drive system actuates and moves the first carrier upwardly away from the carrier inlet 308 as a second carrier passes through the carrier inlet 308 and into carrier receiving space 332. The second carrier is supported by a second pair of carrier support members arranged in an engaged configuration and is also lifted upwardly away from the carrier inlet 308 of the inlet side 302 of the vessel 300. As one or more carriers move upwardly on the inlet side 302, one or more carriers may simultaneously be moving downwardly on the outlet side 304, while one carrier may be passing through the carrier inlet 308, one carrier may be passing through the carrier outlet 310, and one carrier may be moving from the inlet side 302 to the outlet side 304 through the transfer section 352.

As the carriers move upwardly and downwardly through the inlet side 302 and the outlet side 304 of the vessel 300, articles loaded in the carriers may be contacted with at least one fluid. The type of fluid used may depend at least in part on the type of article being heated. In one implementation, the fluid may be or include water. The fluid may also be or include other liquids and/or gases including, but not limited brines, oils, propylene glycol, food grade, and various heat transfer fluids. In the preheat section 102 (shown in FIGS. 1A-1B), the temperature of the fluid used to contact the articles may be higher than the average or minimum temperature of each of the articles by various amounts. For example and without limitation, in certain implementations, the temperature of the fluid may exceed the average or minimum temperature of the article by at least about 1° C., at least about 2° C., at least about 5° C., at least about 8° C., at least about 10° C., at least about 15° C., at least about 20° C., at least about 25° C., or at least about 30° C. Overall, the temperature of the fluid can be, among other temperatures, at least about 25° C., at least about 30° C., at least about 35° C., at least about 40° C., at least about 45° C., at least about 50° C., at least about 55° C., or at least about 60° C. In certain implementations the fluid may not be more than about 100° C., not more than about 95° C., not more than about 90° C., not more than about 85° C., not more than about 80° C., not more than about 75° C., not more than about 70° C., not more than about 65° C., or not more than about 60° C.

The fluid contacting the articles can be in various forms. In some cases, contacting may be through at least partial submersion in a liquid bath of the fluid. In other cases, the fluid may be provided as a spray and the contacting step may include discharging streams of fluid onto one or more surfaces of the articles. When provided as a spray, the fluid may be provided in the form of a liquid, a gas, or a combination thereof. In some cases, the fluid may be in the form of both a spray and a liquid bath. For example, submerged articles passing through a liquid bath may also be contacted with jets of pressurized fluid. Alternatively, jets of fluid may be submerged in the liquid bath such that the jets create turbulent flow or otherwise agitate the liquid bath without the jets contacting the articles. It should be appreciated that the fluid of the liquid bath may be different than the sprayed fluid. Moreover, to the extent each of the inlet side 302 and the outlet side 304 are partially filled with fluid and/or are configured to have fluid sprayed therein, the fluid or fluids used in the inlet side 302 may differ from those used in the outlet side 304.

When at least a portion of the fluid used to contact the articles is in the form of a spray, the vessel 300 may further include one or more nozzles (not shown) for discharging pressurized fluid and corresponding fluid conduits for providing fluid to the one or more nozzles. Each of the nozzles may be configured to discharge fluid at a particular pressure or at a range of pressures. For example, among other pressures, the fluid may be discharged at a pressure of at least about 20 psig, at least about 25 psig, at least about 30 psig, at least about 35 psig, at least about 40 psig, at least about 45 psig, at least about 50 psig, at least about 55 psig, at least about 60 psig, at least about 65 psig, or at least about 70 psig toward the loaded articles.

In general, heating of the article in the vessel 300 may be achieved using fluid in the form of either a liquid bath and/or a spray. However, in certain implementations, a spray configuration may have particular advantages. Among other things, nozzles may be directed or otherwise configured to focus spray particular areas of an article or a carrier whereas a liquid bath generally results in at least partial submersion of an article or carrier. So, for example, nozzles may be used to direct fluid to different portions of an article that may contain different foodstuffs or otherwise have different thermal properties. Similarly, multiple types of articles may be loaded into a single carrier and nozzles may be used to selectively spray only a subset of the loaded articles or to spray different subsets of the articles with a fluid at different temperatures or different fluids.

The articles loaded into the carriers being transported through the vessel 300 may be contacted with a first fluid as the carrier passes upwardly through the inlet side 302 of the vessel 300 (e.g., through the carrier receiving space 332) and may be contacted with a second fluid as the carrier passes downwardly through the outlet side 304 of the vessel 300 (e.g., through the carrier receiving space 334). The temperatures of the two fluids can be substantially the same (e.g., within less than 10° C., within less than about 5° C., within less than about 2° C., or within less than about 1° C. of each other) or substantially different (e.g., at least 10° C. different from each other). In certain implementations, different fluid temperatures may be used to perform multi-stage heating where the article is first heated to a first temperature in the inlet side 302 and subsequently heated to a second temperature in the outlet side 304. As a result, the temperature of the article is ultimately raised to the second temperature, but may spend less overall time at the elevated temperature. In some cases, the temperature of the first fluid can be at least about 5° C., at least about 10° C., at least about 15° C., at least about 20° C., at least about 25° C., or at least about 30° C. and/or not more than about 50° C., not more than about 45° C., not more than about 40° C., not more than about 35° C., not more than about 30° C., not more than about 25° C., not more than about 20° C., not more than about 15° C., or not more than about 10° C. different than the temperature of the second fluid. As used herein, the term "different" can refer to a value that is higher or lower than another value.

Additionally, or in the alternative, the first and second fluids used to contact the articles on the inlet side 302 and the outlet side 304, respectively, can be different types of fluids and/or be in different forms. For example, in some cases, the first fluid used to contact the articles in the inlet side 302 may be in the form of a spray and the second fluid used to contact the articles in the outlet side 304 may be in the form of a liquid bath. Articles loaded in carriers passing through the transfer section 352 may or may not be contacted with a fluid.

Vessels in accordance with the present disclosure, such as the vessel 300, may have any suitable size and/or shape and can be formed from a material that provides sufficient strength and durability, while being inert to the internal contents of the vessel at the prescribed operating conditions. In some cases, the vessel 300 may have a general rectangular prism shape, as shown in FIGS. 3A and 3B, and can include a pair of broader sidewalls 366, 368 spaced apart from a pair of narrower end walls 370, 372 (each indicated in FIG. 3A, with sidewall 368 being transparent to illustrate the internal components of the vessel 300). The sidewalls 366, 368 and/or the end walls 370, 372 may be formed from a plurality of panels, one or more of which may be removable. Such removable panels may, for example, facilitate maintenance and minimize equipment downtime to maximize overall production.

In certain implementations of the present disclosure, upon exiting the preheat section 102, each article can have a minimum temperature, measured at its coldest point, that may be, but is not limited to, at least about 25° C., at least about 30° C., at least about 35° C., at least about 40° C., at least about 45° C., at least about 50° C., at least about 55° C., at least about 60° C., at least about 65° C., at least about 70° C., at least about 75° C., at least about 80° C., or at least about 85° C. Alternatively, or in addition, the minimum temperature of each article withdrawn from the preheat section 102 measured at its coldest point, may be not more than about 105° C., not more than about 100° C., not more than about 95° C., not more than about 90° C., not more than about 85° C., not more than about 80° C., not more than about 75° C., not more than about 70° C., not more than about 65° C., not more than about 60° C., not more than about 55° C., not more than about 50° C., or not more than about 45° C.

Although described herein and illustrated in FIGS. 3A and 3B as being positioned near a lower vertical end 311, it should be appreciated that in other implementations of the present disclosure, the vessel 300 may be arranged such that the inlet 308 and the outlet 310 may be positioned at other locations. For example, in one implementation, each of the inlet 308 and the outlet 310 may instead be disposed at an upper vertical end 315 of the vessel 300. In such implementations, the general operation of the vessel 300 may transport carriers through a "U"-shaped path as opposed to the inverted "U"-shaped path discussed above. More specifically, carriers may be transported vertically downward through the inlet side 302 of the vessel 300 and vertically upward through the outlet side 304 of the vessel 300.

Turning again to FIGS. 1A and 1B, when the preheat section 102 and the heating section 104 may operate at different pressures, the articles exiting the preheat section 102 may be passed through a pressure change section 114 before entering the heating section 104. When used, the pressure change section 114 may be any zone or section configured to transition the carrier from two areas of different pressure. In certain implementations and without limitation, the difference in pressure between the two areas may be, in certain implementations and without limitation, at least about 1 psig, at least about 5 psig, at least about 10 psig, or at least about 12 psig and/or not more than about 75 psig, not more than about 50 psig, not more than about 40 psig, or not more than about 35 psig.

In certain implementations, all or a portion of the hold section 106 and/or the cooling section 108 may be operated at a different pressure than the heating section 104. To facilitate such pressure differences, pressure change sections may be disposed between sections of the heating system 100. For example, the heating system 100 includes a first pressure change section 114 between the preheat section 102 and the heating section 104 and a second pressure change section 115 between the high pressure cooling section 110 and the low pressure cooling section 112. The pressure change sections 114, 115 may, for example, be in the form of a pressure or air lock configured to receive a carrier from a first environment at a first pressure, close or otherwise seal, increase (or decrease) pressure within the pressure change section to that of a second environment, and then transfer the carrier to the second environment. The placement of the pressure change sections 114 and 115 are provided as one example placement of pressure change sections within heating systems of the present disclosure. More generally, pressure change sections may be disposed between any two sections or sub-sections of the heating system 100 in which the sections are maintained or operated at different internal pressures. Pressure change sections may also be disposed between pressurized sections and unpressurized or atmospheric portions of the heating system 100. So, for example, a pressure change section may be disposed downstream of the heating section 104 between the heating section and one of the hold section 106 or the cooling section 108 (or any section of the cooling section 108). In some cases, multiple adjacent pressure change sections may be used to provide a stepped decrease or increase in pressure. Various examples of suitable configurations of the pressure change sections 114, 115 are described in the '590 Patent.

Referring back to FIGS. 1A and 1B, the carriers exiting the preheat section 102 and passed through the pressure change section 114, may then be introduced into a heating section 104, wherein the articles may be rapidly heated using microwave energy. In addition to microwave energy, the heating section 104 may also employ other types of heating, such as, for example, conductive or convective heating for further increasing the temperature of the articles passing therethrough. In implementations of the present disclosure, the majority of energy used to heat the articles may be microwave energy. The microwave energy may heat the articles directly and/or may be used to heat the fluid surrounding the articles, which may further heat the articles by convection and/or conduction.

As the carrier passes through the heating section 104, the articles may enter a heating chamber 105 where they are heated so that the coldest portion of each article achieves a target temperature. When the heating system 104 is a sterilization or pasteurization system, the target temperature can be a sterilization or pasteurization target temperature. Such a temperature may be, but is not limited to, at least about 65° C., at least about 70° C., at least about 75° C., at least about 80° C., at least about 85° C., at least about 90° C., at least about 95° C., at least about 100° C., at least about 105° C., at least about 110° C., at least about 115° C., at least about 120° C., at least about 121° C., or at least about 122° C. and/or not more than about 130° C., not more than about 128° C., or not more than about 126° C.

As the articles pass through the heating section 104, they may be heated to the target temperature in a relatively short time, which can help minimize any damage or degradation of the articles. For example, the average residence time of each article passing through the heating section 104 may be at least about 5 seconds, at least about 20 seconds, or at least about 60 seconds and/or not more than about 10 minutes, not more than about 8 minutes, not more than about 5 minutes, not more than about 3 minutes, not more than about 2 minutes, or not more than about 1 minute. During residence in the heating section 104, the minimum temperature of the articles heated in the heating section 104 may increase by a particular amount. For example, in certain implementations of the present disclosure, the minimum temperature of the articles can increase by at least about 20° C., at least about 30° C., at least about 40° C., at least about 50° C., or at least about 75° C. and/or not more than about 150° C., not more than about 125° C., or not more than about 100° C.

When the heating section 104 is at least partially filled with a fluid to form a liquid bath, the average bulk temperature of the fluid forming the liquid bath in the heating section 104 may vary and, in some cases, can depend on the amount of microwave energy discharged into the heating section 104. For example, and without limitation, the average bulk temperature of the fluid in the heating section 104 can be at least about 70° C., at least about 75° C., at least about 80° C., at least about 85° C., at least about 90° C., at least about 95° C., at least about 100° C., at least about 105° C., at least about 110° C., at least about 115° C., or at least about 120° C. and/or not more than about 135° C., not more than about 132° C., not more than about 130° C., not more than about 127° C., or not more than about 125° C. In some cases, this can be at least about 1° C., at least about 2° C., at least about 5° C., at least about 10° C., at least about 15° C. and/or not more than about 50° C., not more than about 45° C., not more than about 40° C., not more than about 35° C., not more than about 30° C., or not more than about 25° C. different (e.g., higher or lower) than the temperature of the article measured at its coldest point.

In certain implementations, the heating chamber 105 can be operated at approximately ambient pressure. Alternatively, the heating chamber 105 may be pressurized such that it operates at a pressure that is above ambient pressure. For example, in certain implementations the heating chamber 105 may operate at least 5 psig, at least about 10 psig, at least about 15 psig, or at least about 17 psig and/or not more than about 80 psig, not more than about 60 psig, not more than about 50 psig, or not more than about 40 psig above ambient pressure. As used herein, the term "ambient" pressure refers to the pressure exerted by the fluid in the heating chamber 105 without the influence of external pressurization devices.

Figure 4:
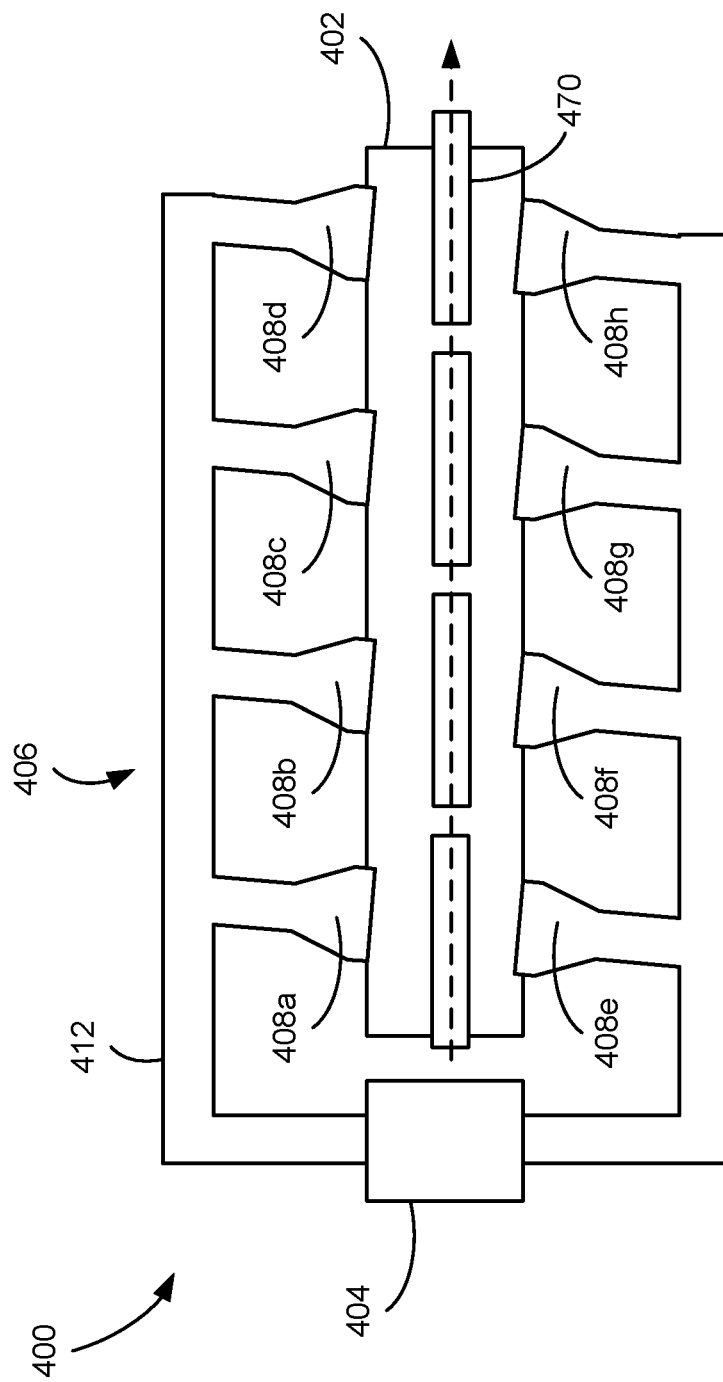
FIG. 4 is a first schematic illustration of an example heating section of the heating system of FIGS. 1A and 1B and depicts elements for providing microwave energy to the heating section.

One example of a heating section 400 configured for use in implementations of heating system described herein is shown schematically in FIG. 4. The heating section 400 generally includes a heating chamber 402, at least one generator 404 for generating microwave energy, such as microwave energy, and a distribution system 406 for directing at least a portion of the energy from the generator 404 (or generators) to the heating chamber 402. The heating section 400 further includes one or more launchers 408a-h for discharging microwave energy into the interior of the heating chamber 402, and a convey system 410 for passing carriers, such as carrier 470, loaded with articles through the heating chamber 402.

The generator 404 can be any suitable device for generating microwave energy of a desired wavelength (A). Examples of suitable types of generators can include, but are not limited to, magnetrons, klystrons, traveling wave tubes, and gyrotrons. Although illustrated in FIG. 4 as including a single generator 404, it should be understood that the heating section 400 may include any number of generators arranged in any suitable configuration. For example, in certain implementations, the heating section 400 may include at least 1, at least 2, at least 3 and/or not more than 5, not more than 4, or not more than 3 microwave generators. Specific configurations of various microwave heating sections including various numbers of generators are discussed in the '590 Patent.

The distribution system 406 includes a plurality of waveguides, such as waveguide 412, for directing the microwave energy from the generator 404 (or generators) to the heating chamber 402. The waveguides can be constructed to propagate microwave energy in a specific predominant mode, which may be the same as or different than the mode of microwave energy generated by the generator. As used herein, the term "mode" refers to a generally fixed cross-sectional field pattern of microwave energy. Examples of suitable modes of microwave energy are $TE_{xy}$ mode, wherein x and y are integers in the range of from 0 to 5 and $Tm_{ab}$ mode, wherein a and b are integers in the range of from 0 to 5.

The heating section 400 further includes at least one launcher, such as launchers 408a-h, for discharging microwave energy into the heating chamber 402. When the heating section 400 includes two or more launchers, at least some of the launchers may be positioned on the same side of the heating chamber 402. For example, as illustrated in FIG. 4, launchers 408a-d are disposed on a first side 414 of the heating chamber 402, while launchers 408e-h are disposed on a second side 416 of the heating chamber 402 opposite the first side 414. The same-side launchers may be axially spaced from one another along the length of the heating chamber 402, and, in certain implementations, may be distributed along a direction parallel to the direction of travel of the carrier 470 passing through the chamber 402, as shown in FIG. 4. The heating section 400 may also include two or more same-side launchers that are laterally spaced from one another in a direction generally perpendicular to the direction of travel of the carriers through the heating chamber 402. Additionally, or in the alternative, the heating section 400 may also include at least two launchers positioned on opposite sides of the heating chamber 402. These opposed or oppositely disposed launchers may be oppositely facing, such that launch openings of the launchers are substantially aligned, as shown in FIG. 4, or staggered such that the launch openings of opposed launchers are axially and/or laterally spaced from each other. Several specific launchers and various configurations of multiple launchers suitable for use in the microwave heating section of implementations of the present disclosure are described in further detail in the '590 Patent.

Any suitable type of launcher may be used in the heating section 400. In some cases, one or more launchers 408a-h utilized in the heating section 400 may be tilted at a launch tilt angle. In certain implementations, for example, the launch tilt angle may be one of at least 2°, at least about 4°, at least about 6° and/or not more than about 15°, not more than about 10°, not more than about 8°, or not more than about 6°, as described in detail in the '590 Patent. Additionally, or in the alternative, at least one launch opening may be at least partially covered with a microwave-transparent window, as also described in detail in the '590 Patent. Specific examples of suitable launcher configurations, including particular dimensions, shapes, and orientations, are also described in the '590 Patent.

Each launcher 408a-h may be configured to emit a certain amount of microwave energy into the heating chamber 402. For example, in certain implementations, each launcher 408a-h may be configured to emit at least about 5 kW, at least about 7 kW, at least about 10 kW, at least about 15 kW and/or not more than about 50 kW, not more than about 40 kW, not more than about 30 kW, not more than about 25 kW, not more than about 20 kW, or not more than about 17 kW. When the heating section 400 includes two or more launchers, each launcher may emit the same amount of energy as one or more other launchers, or at least one launcher may emit a different (e.g., lower or higher) amount of energy, as compared to at least one of the other launchers. In certain implementations, the launchers 408a-h may be configured to discharge a particular amount of overall energy into the heating chamber 402. For example, and without limitation, the overall energy discharged into the heating chamber 402 may be at least about 25 kW, at least about 30 kW, at least about 35 kW, at least about 40 kW, at least about 45 kW, at least about 50 kW, at least about 55 kW, at least about 60 kW, at least about 65 kW, at least about 70 kW, or at least about 75 kW and/or not more than about 100 kW, not more than about 95 kW, not more than about 90 kW, not more than about 85 kW, not more than about 80 kW, not more than about 75 kW, not more than about 70 kW, or not more than about 65 kW.

Figure 5:
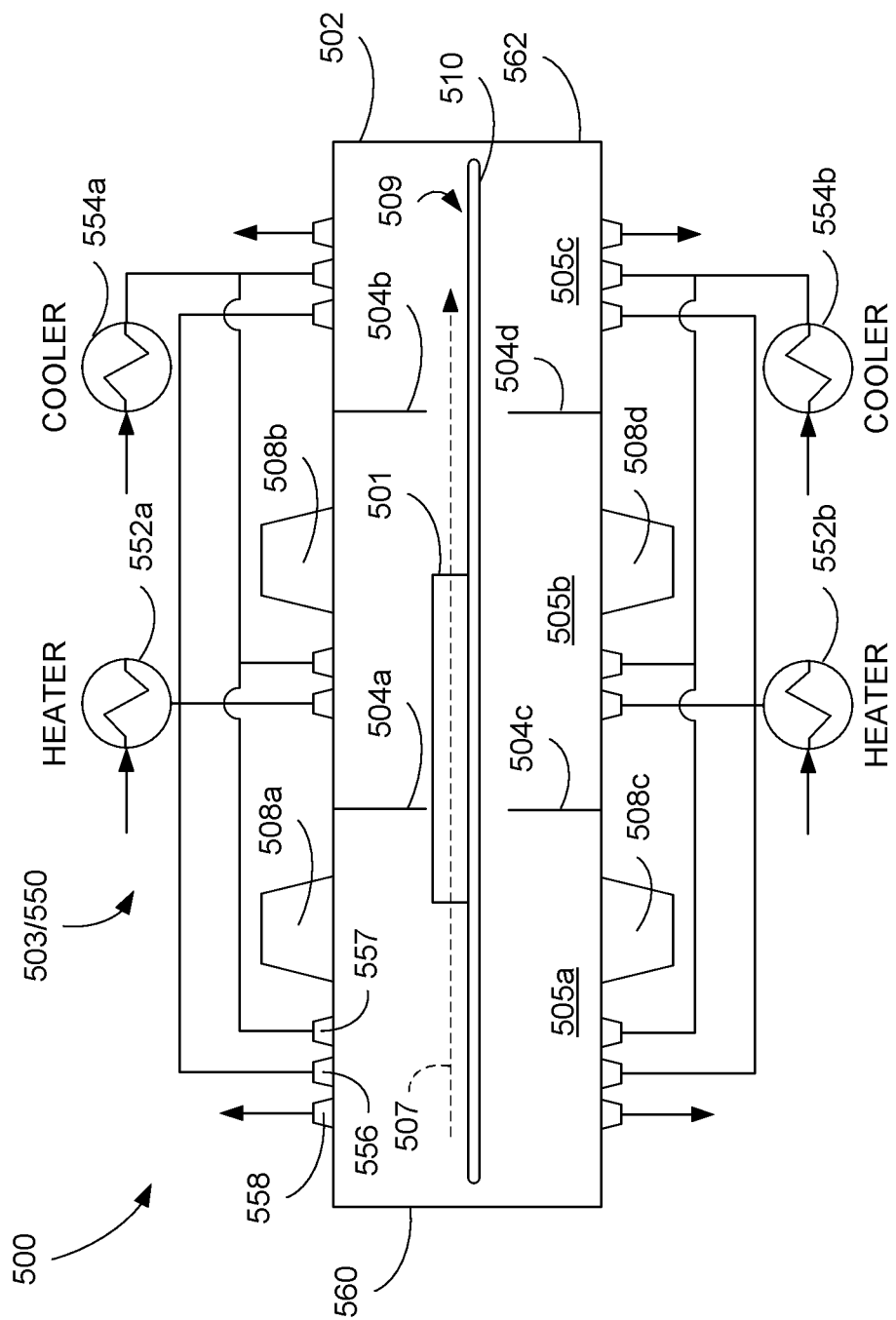
FIG. 5 is a second schematic illustration of the heating section of the heating system of FIGS. 1A and 1B and depicts elements for providing control of fluids within the heating section.

In certain implementations, the heating chamber may be at least partially filled with a fluid medium and the heating section may further include a temperature control system that in combination with a fluid distribution system for controlling the temperature of the fluid medium within the heating chamber. The fluid distribution system may include one or more heat exchangers for heating and/or cooling the fluid and a plurality of nozzles for discharging and/or removing fluid from the heating chamber. One example of a heating section 500 including a heating chamber 502, a temperature control system 503 and a fluid distribution system 550 is illustrated in FIG. 5. As shown in FIG. 5, the heating section 500 further includes multiple microwave launchers 508a-d. An example carrier 501 is also included in FIG. 5 and is indicated as travelling in a convey direction 507 by a convey line 510. The microwave launchers 508a-d are illustrated in FIG. 5 as being perpendicular to the convey direction 507 and the convey line 510, however, as previously discussed in the context of FIG. 4, above, in certain implementations the microwave launchers 508a-d may also be disposed at a non-perpendicular angle relative to the convey direction 507.

As shown in FIG. 5, the temperature control system 502 may include a plurality of dividers, such as baffles 504a-d, for further controlling the fluid temperature within the heating chamber 502. More specifically, such dividers may reduce the cross-sectional area between adjacent temperature zones to reduce exchange of fluid between the zones. In some cases, the baffles 504a-d may include pairs of opposing baffles extending from each of a top and bottom of the heating chamber 502 as shown in FIG. 5. The baffles 504a-d may be used to define separate temperature zones 505a-c along the length of the heating chamber 502. As illustrated in FIG. 5, for example, the baffles 504a-d may be disposed between adjacent launchers (e.g., baffle 504a is disposed between adjacent launchers 508a and 508b) and spaced apart along the length of the heating chamber 502. The baffles 504a-d may extend into interior of the heating chamber 502 toward a convey line 510 extending through the heating chamber 502 so that the baffles 504a-d define an opening through which the carriers, such as carrier 570, transported along the convey line 510 may pass. In some cases, the size of the opening may be only slightly larger than the height of the carrier 570 so that the opening easily permits the carrier 570 to pass through while minimizing the amount of fluid passing between adjacent temperature zones of the heating chamber 502.

The fluid distribution system 550 shown in FIG. 5 includes a pair of heaters 552a-b and a pair of coolers 554a-b configured to heat and cool streams of fluid and a plurality of spaced-apart nozzles pairs configured to discharge the heated and cooled fluid into the heating chamber 502. In the example shown in FIG. 5, each pair of nozzles includes a nozzle for discharging heated fluid into the heating chamber 502 such as nozzle 556, and a nozzle for discharging cooled fluid into the heating chamber 502, such as nozzle 557. In general, each of the heated and cooled fluid may be used to maintain a particular temperature or temperature range within each of the temperature zones 505a-c. For example, certain temperature zones may be prone to heat loss and a corresponding decrease in temperature and may be provided with heated fluid to offset such changes in temperature. As another example, fluid within a temperature zone may absorb microwave energy emitted from the launchers of the heating chamber and, as a result, may gradually increase in temperature. Such temperature zones may be regulated by a supply of cooled fluid.

In the implementation of FIG. 5, pairs of same-side nozzles are spaced apart from one another along the length of the heating chamber 502 while pairs of oppositely-disposed nozzles are shown as being generally aligned with each other. In other implementations, the microwave heating section 500 may only include same-side nozzle pairs and/or the pairs of oppositely-disposed nozzles may be staggered from one another along the length of the heating chamber 502. Additionally, as shown in FIG. 5, one or more withdrawal nozzles (e.g., withdrawal nozzle 558) may also be present for withdrawing fluid from the heating chamber 502. The withdrawn fluid may be returned to one of the heaters 552a-b or coolers 554a-b before being reintroduced into the heating chamber 502.

The temperature control system 503 and the fluid distribution system 550 described herein can be used to selectively introduce heated and/or cooled fluid into the heating chamber 502 to maintain a desired fluid temperature profile along the length of the heating chamber 502. Streams of heated and cooled fluid may be added simultaneously or one or the other may be added separately. Alternatively, or in addition, fluid may also be removed from the chamber 502 to achieve a desired temperature. Fluid may be removed from the chamber 502 during or separate from addition of the heated and/or cooled fluid streams.

The temperature and/or flow rates of the heated and cooled streams may vary. For example and without limitation, in some cases the temperature of the heated fluid can be at least about 35° C., at least about 40° C., at least about 45° C., at least about 50° C., at least about 55° C., at least about 60° C., at least about 65° C., at least about 70° C., or at least about 75° C. and/or not more than about 100° C., not more than about 95° C., not more than about 90° C., not more than about 85° C., not more than about 80° C., not more than about 75° C., not more than about 70° C., not more than about 65° C., not more than about 55° C., or not more than about 50° C. The temperature of the cooled fluid may similarly vary in implementations of the present disclosure. For example and without limitation, in some cases the cooled fluid may be at least about 20° C., at least about 25° C., at least about 30° C., or at least about 35° C. and/or not more than about 45° C., not more than about 40° C., or not more than about 35° C.

In some cases, the difference between the temperature of the heated fluid stream and the temperature of the cooled fluid stream may similarly vary. For example and without limitation, in some cases the heated fluid stream and the temperature of the cooled fluid stream may be between at least about 10° C., at least about 15° C., at least about 20° C., at least about 25° C., at least about 30° C., or at least about 35° C. and/or not more than about 70° C., not more than about 65° C., not more than about 60° C., not more than about 55° C., not more than about 50° C., or not more than about 45° C. Additionally, the amount by which temperature of the heated or cooled fluid differs from the average bulk temperature of the fluid within the heating chamber 502 may similarly vary. For example and without limitation, in some cases the difference may be at least about 2° C., at least about 3° C., at least about 5° C., at least about 10° C., at least about 15° C., or at least about 20° C. and/or not more than about 45° C., not more than about 40° C., not more than about 35° C., not more than about 30° C., not more than about 25° C., not more than about 20° C., not more than about 15° C., or not more than about 10° C.

In operation, the timing and amount of the addition of a heated or cooled fluid into the heating chamber 502 may be determined by first measuring at least one fluid temperature within the heating chamber 502. The fluid temperature can be, among other things, the average bulk temperature of the fluid at an inlet 560 of the heating chamber 502, the average bulk temperature of the fluid at an outlet 562 of the heating chamber 502, the average bulk temperature of the fluid at some point between the inlet 560 and the outlet 562 of the heating chamber 502, or any combinations thereof.

In certain implementations, once measured, the value of the measured temperature may be compared with a target value for the temperature at the location of the measurement to determine a difference. If the difference is larger than a maximum allowable difference, heated or cooled fluid may be selectively added into the heating chamber 502, or fluid may be withdrawn from the heating chamber 502 until the difference is lower than the maximum allowable difference, at which point the addition or withdrawal of fluid may be stopped. The maximum allowable difference may vary in implementations of the present disclosure. For example and without limitation, in some cases the maximum allowable difference can be a difference in temperature of not more than about 5° C., not more than about 4° C., not more than about 3° C., not more than about 2° C., not more than about 1.5° C., or not more than about 1° C., or it can be a percentage difference, such as, for example, not more than about 10 percent, not more than about 8 percent, not more than about 6 percent, not more than about 5 percent, not more than about 4 percent, not more than about 2 percent, or not more than about 1 percent different than the target value.

In some cases, when heated and cooled fluid streams are added simultaneously, or nearly simultaneously, one of the streams may be added at a higher flow rate than the other. As used herein, the term "cooled" may simply mean cooler relative to the heated stream and may not necessarily involve active cooling. When the system includes nozzles spaced apart from one another along the length of the heating chamber 502, the operation of a first nozzle or first group of nozzles may be different than another nozzle or group of nozzles located further up- or downstream from the first nozzle or group of nozzles. This may be needed to achieve a desired temperature profile across the entire heating chamber 502. For example, in some cases, the ratio of the volumetric flow rate of fluid added to fluid withdrawn from the heating chamber 502 may be larger nearer the inlet 560 of the heating chamber 502, while the ratio of fluid added to fluid withdrawn may be smaller near the outlet 562 of the heating chamber 502. The addition and removal of fluid to and from the heating chamber 502 may be done manually or with an automatic control system.

In some cases, the temperature control system 503 and the fluid distribution system 550 may be operated to maintain a temperature profile in which the temperature of the fluid at the outlet 562 of the heating chamber 502 ($T_F$) may be warmer than the temperature of the fluid at the inlet 560 ($T_O$). A graphical depiction of such a temperature profile is provided in FIG. 6. The temperature profile of FIG. 6 does not represent an exact temperature profile across the heating chamber 502, but rather is intended merely as an example profile that illustrates an overall trend across the heating chamber 502.

The temperature difference between the fluid at the inlet 560 and the outlet 562 of the heating section 500 may vary in implementations of the present disclosure. In certain implementations, for example, the heating section 500 may be divided into multiple separate temperature zones along its length, with each successive temperature zone increasing in temperature to facilitate more gradual heating of articles. For example and without limitation, in some cases the temperature of the fluid at the outlet 562 of the heating chamber 502 can be warmer than the temperature of the fluid at the inlet by at least about 10° C., at least about 15° C., at least about 20° C., at least about 25° C., at least about 30° C., at least about 35° C., at least about 40° C., at least about 45° C., at least about 50° C., or at least about 55° C. and/or not more than about 90° C., not more than about 85° C., not more than about 80° C., not more than about 75° C., not more than about 70° C., not more than about 65° C., not more than about 60° C., or not more than about 55° C. Similarly, the temperature of the fluid at the inlet 562 and the temperature of the fluid at the outlet 560 may similarly vary. For example and without limitation, in some cases the temperature of the fluid at the inlet 560 can be at least about 35° C., at least about 40° C., at least about 45° C., at least about 50° C., at least about 55° C., or at least about 60° C. and/or not more than about 85° C., not more than about 80° C., not more than about 75° C., not more than about 70° C., not more than about 65° C., or not more than about 60° C., while the outlet fluid temperature can be at least about 50° C., at least about 55° C., at least about 60° C., at least about 65° C., at least about 75, at least about 80° C., at least about 85° C., at least about 90° C., at least about 95° C., at least about 100° C., at least about 105° C., at least about 110° C., or at least about 115° C. and/or not more than about 130° C., not more than about 125° C., not more than about 120° C., not more than about 115° C., or not more than about 110° C.

Figure 6:
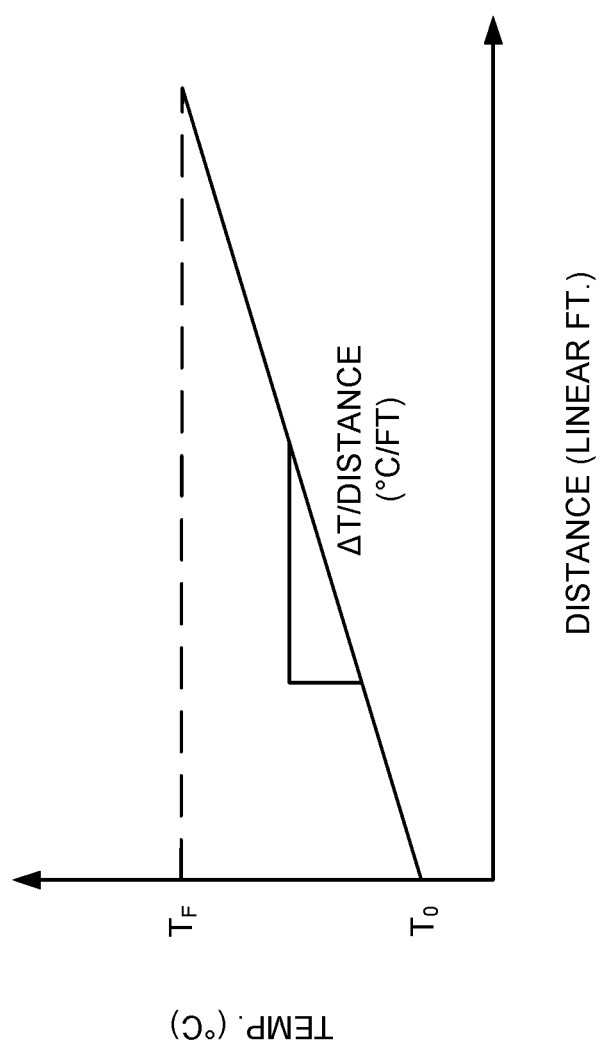
FIG. 6 is a graphical representation of a fluid temperature profile that may be provided in the heating section of the heating system of FIGS. 1A and 1B.

The change in temperature per linear foot (ΔT/ft) of the fluid across the length of the heating chamber 502 may vary or it may remain substantially constant, as is the case illustrated in the example of FIG. 6. As used herein, the term "substantially constant" means that the value of the change in temperature per linear foot varies by not more than about 50 percent at any point along the length of the heating chamber 502. The change in temperature per linear foot along the length of the heating chamber 502 may vary. For example and without limitation, in some cases the change in temperature per linear foot along the length of the heating chamber 502 may be at least about 0.50° C./ft, at least about 1° C./ft, at least about 1.5° C./ft, at least about 2° C./ft, at least about 2.5° C./ft, at least about 3° C./ft, at least about 3.5° C./ft, at least about 4° C./ft, at least about 4.5° C./ft, at least about 5° C./ft, at least about 5.5° C./ft, or at least about 6° C./ft and/or not more than about 10° C./ft, not more than about 9.5° C./ft, not more than about 9° C./ft, not more than about 8.5° C./ft, not more than about 8° C./ft, not more than about 7.5° C./ft, not more than about 7° C./ft, or not more than about 6.5° C./ft. When the change in temperature per linear foot remains substantially constant, the overall temperature profile across the heating chamber is generally linear as shown in FIG. 6.

Although temperature and length along the heating chamber 502 are illustrated in FIG. 6 as having an overall linear relationship, it should be appreciated that the actual temperature profile from point to point along the heating chamber 502 may vary. For example, as previously discussed, the heating chamber 502 may be divided into multiple temperature zones 505a-505c, with each temperature zone including one or more launchers and systems for providing fluid to control the temperature within each zone. As a result, the actual temperature along the length of the heating chamber 502 may more accurately be characterized as a series of generally step-wise changes in temperature, with each step corresponding to a different temperature zone 505a-505c The average bulk temperature of the fluid medium is typically higher than the average or minimum temperature of the articles introduced into the heating section, but it may be higher or lower than the target temperature to which the articles are heated (e.g., pasteurization or sterilization temperature). For example and without limitation, in some cases the difference between the average bulk temperature of the fluid medium and the target temperature to which the articles are heated is at least about 1° C., at least about 2° C., at least about 5° C., at least about 10° C., or at least about 15° C. and/or not more than about 45° C., not more than about 40° C., not more than about 35° C., not more than about 30° C., not more than about 25° C., not more than about 20° C., not more than about 15° C., or not more than about 10° C.

Figure 7:
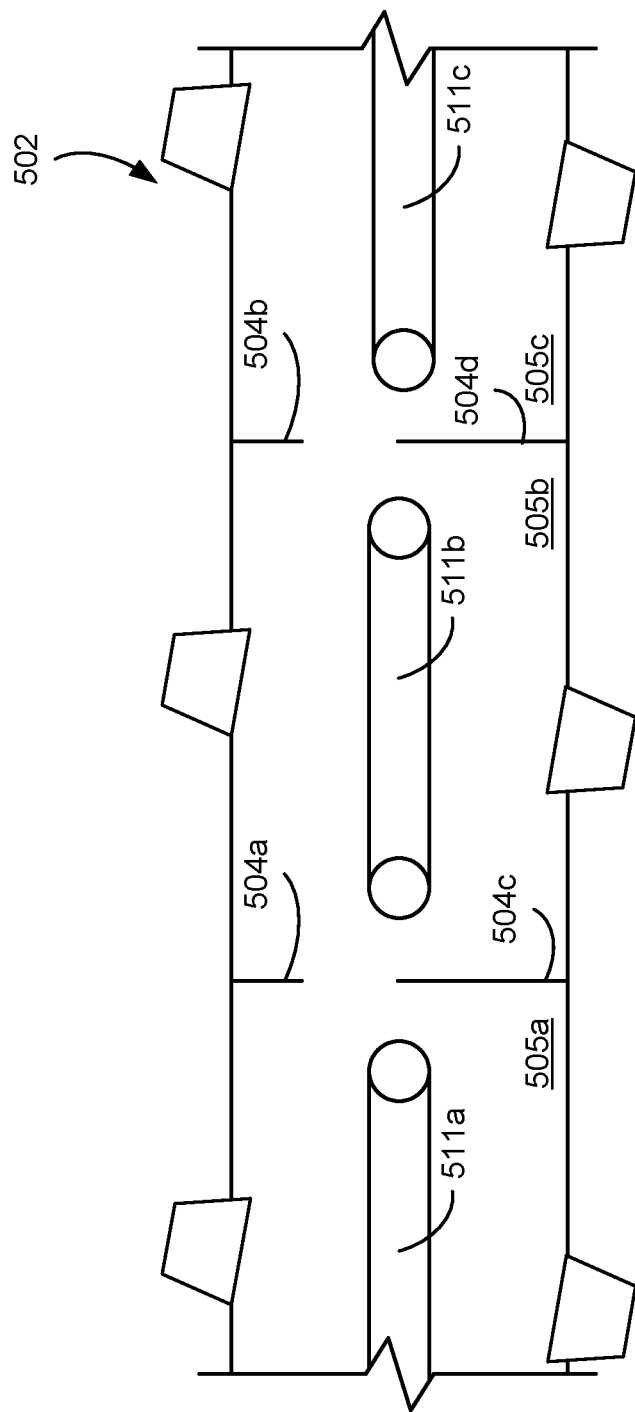
FIG. 7 is a schematic illustration of another example heating section in accordance with the present disclosure.

The heating section 500 can further include at least one conveyor system 509 for transporting the loaded carriers in a convey direction through the heating chamber 502. The conveyor system 509 is configured to receive carriers of preheated articles from the preheat section (e.g., the preheat section 102 of FIGS. 1A and 1B) and to transport such carriers through the heating section 500 as the articles are further heated using microwave energy. In certain applications, the heating section 500 may be pressurized such that the preheated articles may be received from a pressure change section (such as pressure change section 114 of FIGS. 1A and 1B) instead of directly from the preheat section. The conveyor system 509 may, in certain applications, deliver heated carriers to a hold section (e.g., hold section 106 of FIGS. 1A and 1B) within which the articles are held at a hold temperature and for a hold time to achieve pasteurization and/or sterilization. In some cases, the convey line 510 can be a single convey line extending from the inlet 560 to the outlet 562 of the chamber 502. In other cases, such as shown in FIG. 7, the heating section 500 can include two or more individual conveyor segments (e.g., conveyor segments 511a-511c) that are spaced apart from one another in the direction of convey. As shown in FIG. 7, each of the conveyor segments 511a-511c may be disposed in a separate zone (e.g., zones 505a-505c) of the heating chamber 502 and adjacent zones may be separated by baffles (e.g., baffles 504a-504d).

When the heating chamber 502 includes two or more individual, spaced-apart conveyor segments 511a-511c, adjacent conveyor segments may be spaced apart by a distance that is less than the length of the carrier. The heating section 500 may include any suitable number of conveyor segments. For example and without limitation, in some cases the heating section 500 may include at least about 2, at least about 3, at least about 4, or at least about 5 individual conveyor segments and/or not more than about 10, not more than about 8, or not more than about 6 individual conveyor segments, and the length of each segment may be the same as or different than the length of one or more other segments. Each conveyor segment can have a total length less than the length of the heating chamber 502 and the sum of the total lengths of all of the conveyor segments may be less than the total length of the heating chamber 502. The ratio of the total length of the longest conveyor segment to the total length of the heating chamber 502 may also vary. For example and without limitation, the ratio may be not more than about 0.90:1, not more than about 0.85:1, not more than about 0.80:1, not more than about 0.75:1, not more than about 0.70:1, not more than about 0.65:1, not more than about 0.60:1, not more than about 0.55:1, not more than about 0.50:1, not more than about 0.45:1, not more than about 0.40:1, not more than about 0.35:1, not more than about 0.30:1, not more than about 0.25:1, not more than about 0.20:1, or not more than about 0.15:1. In certain implementations, such as illustrated in FIG. 7, each conveyor segment 511a-511c may have a length that is less than a respective one of the temperature zones 505a-505c such that each conveyor segment 511a-511c is disposed between adjacent sets of baffles.

The movement of each individual conveyor segment may be regulated by a driver (not shown), which may be positioned at least partially, or entirely, outside of the interior of the heating chamber 502. Each of the drivers may be individually operable so that the motion of each conveyor segment may be controlled independently of the others. The heating section 500 may further include a synchronization system for synchronizing the movement of each conveyor segment by coordinating the operation of the drivers. Such synchronization can be done manually or automatically using an automatic control system.

In some cases, the carriers may be passed through the heating section 500 using a single-pass heating method that includes moving the carrier 570 from the inlet 560 of the heating chamber 502 directly to its outlet 562 in a single forward direction. Alternatively, the carriers may be passed through the heating section 500 using a multi-pass heating method, which includes passing the carriers in two opposite convey directions (e.g., forward and reverse) so that the carrier is exposed to microwave energy from the same launcher multiple times. For example, in certain implementations a given carrier may be exposed to microwave energy at least three times—once during the initial forward pass, once during the reverse pass, and once again on the second forward pass. This movement may be repeated any number of times and can be done with one or more than one launcher. The multi-pass heating method is described in further detail in U.S. patent application Ser. No. 15/921,921, which is incorporated herein by reference in its entirety to the extent not inconsistent with the present disclosure. In either single- or multi-pass applications, if the heating chamber 502 includes multiple convey segments (such as illustrated in FIG. 7), all or a subset of the conveyor segments may be independently operable. For example, in a single-pass configuration, each conveyor segment may be independently operable such that conveyor segments are selectively activated when receiving or transporting a carrier. Similarly, in multi-pass applications, each conveyor segment may be selectively actuated to operate in either direction to facilitate passing of carriers back and forth a particular launcher.

In some cases, the heating chamber 502 may be formed from a plurality of heating chamber modules removably and selectively coupled to one another using a plurality of fastening devices or similar methods. For example and without imitation, in some cases the heating chamber 502 may be formed from at least 2, at least 3, at least 4, or at least 5 microwave chamber modules coupled together and/nor not more than 10, not more than 8, not more than 6, or not more than 4 individual microwave chamber modules coupled to one another.

Figure 8:
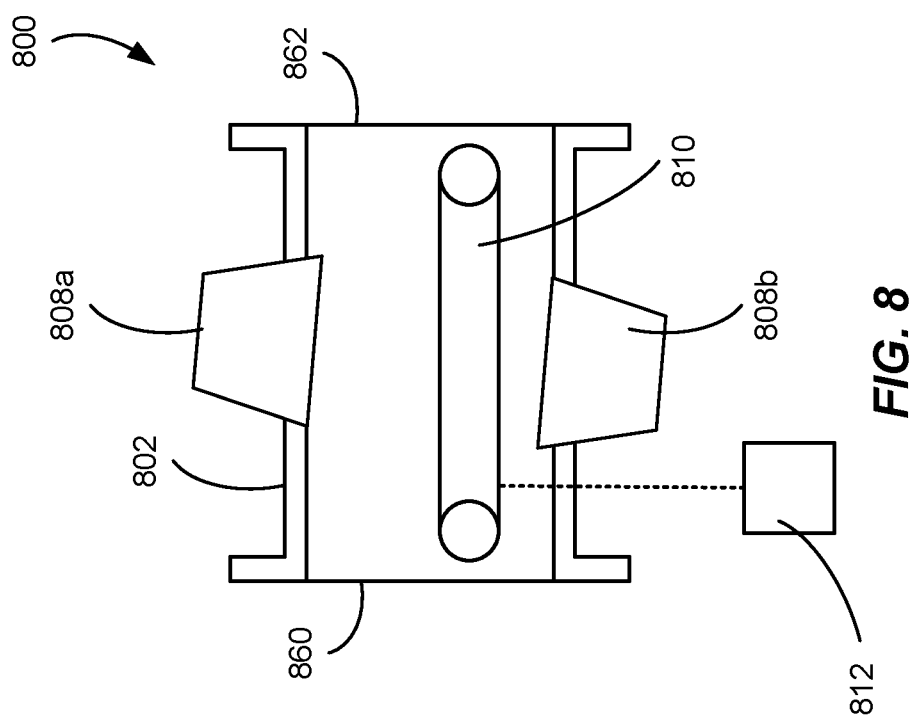
FIG. 8 is a schematic illustration of a heating section module that may be coupled to one or more other similar heating section modules.

One example of a heating chamber module 800 is schematically illustrated in FIG. 8. Each heating chamber module 800 may include a vessel segment 802 including an inlet 860 and an outlet 862, one or more launchers 808a-b for discharging microwave energy into the vessel segment 802, a conveyor segment 810 disposed within the vessel segment 802, and at least one conveyor driver 812 for controlling the movement of the conveyor segment 810. In certain implementations, the vessel segment 802 may be longer than the conveyor segment 810, so that, for example, the ratio of the length of the vessel segment 802 to the length of the conveyor segment 810 is at least about 1.1:1, at least about 1.2:1, at least about 1.3:1, or at least about 1.5:1. In some cases, each heating chamber module 800 may include a pair of launchers 808a-b disposed on the same or opposite sides of the vessel segment 802. The launchers 808a-b may have any suitable design and may be configured as described previously and/or as described in the '590 Patent.

In implementations of the present disclosure including multiple heating chamber modules, each heating chamber module may configured to be independent of the others such that individual heating chamber modules may be selectively coupled and uncoupled from the remainder of the heating chamber modules quickly and easily to minimize downtime for the heating system. Additionally, addition or removal of individual modules from a heating section may permit short-term changes to the overall production rate of the entire system and permit enhanced operational flexibility.

Turning again to FIGS. 1A-B, upon exiting the heating section 104, the carriers may be passed to a hold section 106, wherein the temperature of the articles can be maintained at or above a certain target temperature (a hold temperature) for a particular period of time (a hold time). The specific hold temperature and hold time may vary between applications based on the type of articles being processed, the desired result of such processing (e.g., pasteurization vs. sterilization), and limitations associated with the rate at which articles are to be processed by the heating system 100. For example, in implementations in which articles are processed relatively rapidly, the hold temperature within the hold section 106 may be relatively high and the hold time relatively short to implement a high-temperature short-time (HTST) or "flash" pasteurization process. Alternatively, in implementations in which process time is less critical, the hold time may be extended and the hold temperature reduced such that pasteurization or sterilization occurs over a longer period. For example and without limitation, articles may be maintained in the hold section 106 and the temperature of the coldest part of the articles may be held at a temperature at or above a particular minimum temperature of at least about 70° C., at least about 75° C., at least about 80° C., at least about 85° C., at least about 90° C., at least about 95° C., at least about 100° C., at least about 105° C., at least about 110° C., at least about 115° C., or at least about 120° C., at least about 121° C., or at least about 122° C. and/or not more than about 130° C., not more than about 128° C., or not more than about 126° C. The articles may be held for a period of time (or "holding period") which may vary in different implementations. For example and without limitation, the holding period may be at least about 1 minute, at least about 2 minutes, or at least about 4 minutes and/or not more than about 20 minutes, not more than about 16 minutes, or not more than about 10 minutes. The pressure within the hold section 106 may also vary across application. For example and without limitation, the pressure within the hold section 106 may be at least about 5 psig, at least about 10 psig, at least about 15 psig, or at least about 20 psig and/or not more than about 60 psig, not more than about 55 psig, not more than about 50 psig, not more than about 45 psig, not more than about 40 psig, not more than about 35 psig, or not more than about 30 psig.

Once the heated articles are sufficiently pasteurized or sterilized, the carrier exits the hold section 106 and can then be introduced into a cooling section 108, wherein the articles are rapidly cooled via submersion in a cooled fluid. In certain implementations, for example, the cooling section 108 may reduce the external surface temperature of the articles by at least about 30° C., at least about 40° C., or at least about 50° C. and/or not more than about 100° C., not more than about 75° C., or not more than about 50° C. Such cooling may occur in a time period of at least about 1 minute, at least about 2 minutes, or at least about 3 minutes and/or not more than about 10 minutes, not more than about 8 minutes, or not more than about 6 minutes. Any suitable fluid may be used in the cooling section 108 and, in some cases, the fluid may include a fluid similar to or different than the fluid used in the heating section 104 and/or the hold section 106. In certain implementations and without limitation, when removed from the cooling section 108, the cooled articles can have a temperature of at least about 5° C., at least about 10° C., at least about 15° C., at least about 20° C., at least about 25° C., at least about 30° C. and/or not more than about 40° C., not more than about 35° C., or not more than about 30° C. Once removed from the cooling section 108, the cooled, treated articles can then be removed from the heating system 100 for subsequent storage and/or use.

As shown in FIGS. 1A and 1B, the cooling section 108 may include a high-pressure cooling section 110 and a low-pressure cooling section 112 separated by a pressure change section 115. In certain implementations and without limitation, the pressure of the high-pressure cooling section 110 can be at least about 5 psig, at least about 10 psig, at least about 15 psig, or at least about 20 psig and/or not more than about 60 psig, not more than about 55 psig, not more than about 50 psig, not more than about 45 psig, not more than about 40 psig, not more than about 35 psig, or not more than about 30 psig. Similarly, in certain implementations and without limitation, the pressure of the low-pressure cooling section 112 can be not more than about 15 psig, not more than about 10 psig, not more than about 8 psig, not more than about 5 psig, not more than about 3 psig, or not more than about 2 psig. In some cases and without limitation, the difference in pressure between the high-pressure cooling section 110 and the low-pressure cooling section 112 can be at least about 1 psig, at least about 2 psig, at least about 5 psig, at least about 10 psig, at least about 15 psig, or at least about 20 psig and/or not more than about 60 psig, not more than about 55 psig, not more than about 50 psig, not more than about 45 psig, not more than about 40 psig, not more than about 35 psig, or not more than about 30 psig.

The hold section 106 and/or the cooling section 108 can be at least partially fluid filled. When present, the fluid may be the same as or different than the fluid used in the heating section 104 and/or the preheat section 102. In some cases, the hold section 106 and/or the cooling section 108 may be at least partially fluidly isolated from one another and may, for example, be separated by a carrier transfer section (not shown in FIGS. 1A-B) configured to permit a carrier to pass between the hold section 106 and the cooling section 108. In some cases, the carrier transfer section may be configured to permit only single-stacked (i.e., individual) carriers to pass from the hold section 106 to the cooling section 108 such that the carriers enter the cooling section 108 (such as by entering the high-pressure cooling section 110) one at a time. The transfer section may also be filled with a fluid medium, which can be the same as or different than the fluid medium in either of the hold section 106 or the cooling section 108. For example, in some cases, the fluid medium in the carrier transfer section can be a different temperature and/or pressure than the fluid medium in the hold section 106 and/or the high-pressure cooling section 110. Alternatively, or in addition, the fluid medium in the carrier transfer section may be a different fluid than is present in the hold section 106 and/or the cooling section 108. For example, the carrier transfer section may be filled with air or nitrogen, while the hold section 106 and the cooling section 108 may be filled with water.

The hold section 106 and the cooling section 108 may also be at least partially thermally isolated from one another so that the temperature in one section is significantly different than the temperature in the other section. For example, in some cases, when the hold section 106 and the cooling section 108 each include a fluid medium, the temperature of the fluid in the hold section 106 can be at least about 15° C., at least about 20° C., at least about 25° C., at least about 30° C., at least about 35° C., at least about 40° C., at least about 45° C., at least about 50° C., at least about 55° C., at least about 60° C., at least about 65° C., or at least about 70° C. higher than the temperature of the fluid in the cooling section 108. Additionally, or in the alternative, the temperature of the fluid in the hold section 106 can be not more than about 130° C., not more than about 110° C., not more than about 100° C., not more than about 95° C., not more than about 90° C., not more than about 85° C., not more than about 80° C., not more than about 75° C., or not more than about 70° C. higher than the temperature of the fluid in the cooling section 108.

In certain implementations and without limitation, the temperature of the fluid in the hold section 106 can be at least about 60° C., at least about 65° C., at least about 70° C., at least about 75° C., at least about 80° C., at least about 85° C., at least about 90° C., at least about 95° C., at least about 100° C., at least about 105° C., at least about 110° C., or at least about 115° C. and/or not more than about 130° C., not more than about 125° C., not more than about 122° C., not more than about 120° C., not more than about 115° C., or not more than about 110° C. Similarly, in certain implementations and without limitation, the temperature of the fluid in the cooling section 108 can be not more than about 50° C., not more than about 45° C., not more than about 40° C., not more than about 35° C., not more than about 30° C., or not more than about 27° C.

In some cases, the hold section 106, the cooling section 108, and the carrier transfer section can include three or more individual vessels arranged in series. In other cases, at least a portion of the hold section 106, the cooling section 108, and the carrier transfer section may be present in a single vessel having fluidly and/or thermally-isolated chambers.

Figure 9:
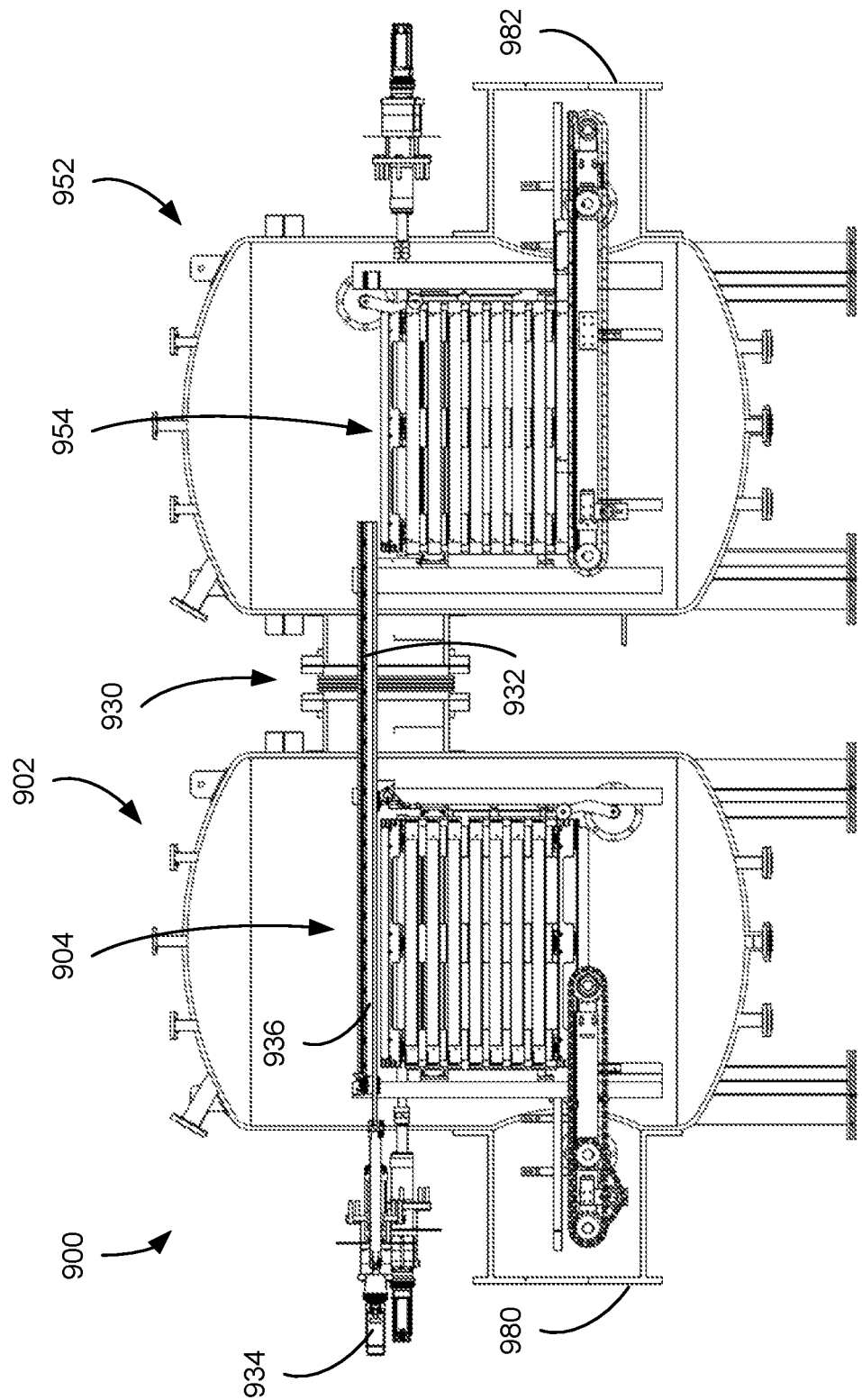
FIG. 9 is a cross-sectional side view of a pressurized vessel for use in the heating system of FIGS. 1A and 1B.

One example of a vessel arrangement 900 suitable for use as holding and cooling sections herein is illustrated in FIG. 9. As shown in FIG. 9, the vessel arrangement 900 includes each of a holding chamber 902 and a cooling chamber 952. The holding chamber 902 may include a first conveyor segment 904 configured to transport several carriers through the holding chamber 902. Similarly, the cooling chamber 952 may include a second conveyor segment 954 to transport several carriers through the cooling chamber 952. The conveyor segments 904, 954 may be arranged to transport the carriers in a vertical direction. For example, the conveyor segments 904, 954 in particular are configured to transport carriers in an upward and downward direction, respectively. In some cases, the conveyor segment 904 in the holding chamber 902 may be configured to transport the carriers upwardly from a carrier inlet 980 and the conveyor segment 954 in the cooling chamber 952 may be configured to transport the carriers downwardly toward a carrier outlet 982. Each of the vertical conveyor segments 904, 954 in the holding chamber 902 and the cooling chamber 952 may be configured similarly to the vertical segments described previously with respect to FIGS. 3A-3D.

As the carriers move upwardly and/or downwardly through the holding chamber 902 and cooling chamber 952, at least a portion of the articles loaded in the carriers may be contacted with at least one fluid. In some cases, the articles may be contacted with a warmed fluid in the holding section 902 and a cooled fluid in the cooling section 952. For example and without limitation, in some cases the difference between the temperature of the warmed and cooled fluids can be at least about 15° C., at least about 20° C., at least about 25° C., at least about 30° C., at least about 35° C., at least about 40° C., at least about 45° C., at least about 50° C., at least about 55° C., at least about 60° C., at least about 65° C., or at least about 70° C. and/or not more than about 130° C., not more than about 110° C., not more than about 100° C., not more than about 95° C., not more than about 90° C., not more than about 85° C., not more than about 80° C., not more than about 75° C., or not more than about 70° C.

In certain cases, the fluid may be in the form of a spray or a fluid bath. In some cases, both a spray and a fluid bath may be used in a single chamber. The method of contacting the articles with a fluid may be the same in both the holding chamber 902 and the cooling chamber 952, or each may employ a different method. In some cases, both the holding chamber 902 and the cooling chamber 952 may include a fluid bath for contacting the articles as the carriers are moved upwardly and downwardly through the respective chambers.

The vessel arrangement 900 may further include a carrier transfer chamber 930 connecting the holding chamber 902 and the cooling chamber 900 of the vessel arrangement 900. The carrier transfer chamber 930 can include a horizontal conveyor segment 932 for transporting the carrier from the upper portion (or other outlet/delivery portion) of the holding chamber 902 to the upper portion (or other inlet/receiving portion) of the cooling chamber. The horizontal conveyor segment 932 may include, for example, a driver 934 at least partially outside the vessel arrangement 900 and at least one device, such as a pusher arm 936 or tab, for guiding the carrier from one end of the carrier transfer chamber 930 to the other. In some cases, the carrier transfer chamber 930 may include at least one weir disposed within the lower portion of the carrier transfer chamber 930 to help ensure that the holding chamber 902 and the cooling chamber 952 are sufficiently thermally and fluidly isolated from one another.

Implementations of the present disclosure may be operated so that the residence time of the loaded carriers in one or more processing zones may be adjusted by, for example, controlling how the carriers are loaded and unloaded from one or more conveyor segments. For example, in certain embodiments, a plurality of carriers loaded with articles may be passed sequentially in a continuous manner from one section of the heating system (e.g., the heating section 104 of FIG. 1) into a first processing section (e.g., the hold section 106 of FIG. 1) and then from the first processing section to a second processing section (e.g., the high-pressure cooling section 108 of FIG. 1), each of the first processing section and the second processing section including respective conveyor segments. In some implementations, each of the conveyor segments can be vertical conveyor segments, such that loaded carriers are transferred by the first conveyor segment and the second conveyor into sequential carrier "slots" defined between adjacent pairs of carrier support members. As previously discussed in the context of FIG. 3D, the carrier-receiving slots may be defined by a vertical conveyor segment with each of the carrier-receiving slots being configured to receive one of the loaded carriers.

The relative residence time between the first processing section and the second processing section may be controlled by varying the rate at which carriers are transported by each conveyor segment. For example, suppose the first processing section and the second processing section each included ten carrier-receiving slots distributed over the same distance. If each of the first conveyor segment and the second conveyor segment are operated at the same speed, the residence time in the first processing section and the residence time in the second processing section would be substantially the same (assuming the first and second conveyor segments were the same length). If, however, the first conveyor segment were to be operated at twice the speed of the second conveyor segment, only every other carrier-receiving slot would receive a carrier and each carrier would spend half as much time in the first conveyor segment as in the second conveyor segment.

Similarly, if the second conveyor segment were to be operated at three times the speed of the first conveyor segment, only every third carrier receiving slot of the second conveyor segment would receive a carrier and the residence time of each received carrier within the second processing section would be one-third of that in the first processing section.

To facilitate the foregoing functionality, each of the first and the second conveyor segments may be incremental conveyor segments. For purposes of the present disclosure, the term "incremental conveyor" or "incremental conveyor segment" is used to refer to a conveyor system that operates by indexing between positions. Such indexing is generally characterized by alternating periods in which the conveyor is moving and paused.

In implementations in which the first and the second conveyor segments are incremental conveyor segments, each of the first and the second conveyor segments may be configured to move a different distance during each index. By doing so, the average speed at which each conveyor moves and the relative residence time in the first and second processing sections may be controlled.

Referring to the first of the previous examples, the first conveyor segment may be configured to index a distance of two carrier-receiving slots per index event while the second conveyor segment may be configured to index a distance of only one carrier-receiving slot. As a result, only every other carrier-receiving slot of the first conveyor segment will be loaded with a slot, while every carrier-receiving slot of the second conveyor segment will receive a carrier. The result for such a configuration is a residence time ratio of 1:2 between the first processing section and the second processing section. Similarly, in the second of the previous examples, the first conveyor segment may be configured to index a distance of only one carrier-receiving slot while the second conveyor segment may index three slots. Doing so would result in a residence time ratio of 3:1.

It should be noted that using the foregoing approach, the relative residence time between the two processing sections and the total combined residence time spent by a carrier in the first and second processing sections may be modified. However, the rate at which carriers enter the first processing section and exit the second processing section remains constant and is dictated by the slowest of the first processing section and the second processing section.

The foregoing principles of operation are now described in further detail in the context of implementations of the present disclosure. As a carrier is passed through the first processing section by the first conveyor segment, it may be moved vertically as discussed in detail previously with respect to FIGS. 3A-3D. After passing through the first processing section, the loaded carriers can be transferred from the first conveyor segment to a second conveyor segment in a second processing section (e.g., the high-pressure cooling section 110 of FIG. 1) by removing the carriers, one by one, from the carrier-receiving slots of the first conveyor segment. In certain implementations, the second conveyor segment can be a linear conveyor, such as a chain conveyor, for sequentially transporting the carriers in a generally horizontal direction, or it can be another vertical conveyor for transporting the carriers in an opposite vertical direction. For example, the second conveyor can be another vertical conveyor and the carriers can be sequentially transitioned from the carrier-receiving slot of the first vertical conveyor and loaded into another carrier-receiving slot of the other vertical conveyor. Thereafter, the carriers can pass sequentially through the second processing section in a continuous manner via the second conveyor segment. In some cases, the second processing section can be the cooling section (e.g., the cooling section 108 of FIG. 1) and the second conveyor segment can be another vertical conveyor segment for transporting the carrier in a generally downward direction. As the carriers are passed through one or both of the first and second processing sections, the carriers may be contacted with a fluid medium. For example, one or both of the first and second processing sections may be at least partially filled with a respective fluid medium to form corresponding liquid baths. Alternatively or in addition to such liquid baths, each processing section may further include nozzles for delivering pressurized sprays or jets of fluid therein.

The average residence time of the carriers in the second processing section can be controlled by changing how the carriers are loaded into and transported by the second conveyor segment. In particular, it is possible to adjust the average residence time of the loaded carriers in the second processing section ($T_2$) relative to the average residence time of the loaded carriers in the first processing sections ($T_1$) by periodically skipping one or more carrier-receiving slots of the respective conveyor segments when loading the carriers onto or unloading the carriers from the conveyor segment. For example, when each of the carrier-receiving slots of a first conveyor segment are sequentially loaded with a carrier and the conveyor segment is incrementally actuated such that the carriers move incrementally through a first processing section, the residence time of each carrier in the second processing section may be equal to the maximum residence time achievable in that section. The residence time of the carriers may be changed by, for example, varying the speed at which the second conveyor segment moves during at least a portion of the movement of the first conveyor segment. As a result, one or more carrier-receiving slots of the second conveyor segment may be "skipped" resulting in a change in the average residence time of the carriers.

When more carrier-receiving slots are skipped, the residence time in the second processing section decreases, and when fewer carrier-receiving slots are skipped, the residence time in the second processing section increases. As more or fewer carrier-receiving slots are skipped, the residence time can be changed (e.g., increased or reduced) incrementally by an amount equal to a multiple of the residence time per carrier-receiving slot. The residence time per carrier-receiving slot is calculated by dividing the maximum residence time in the second processing section by the maximum number of carrier-receiving slots in the second conveyor segment. As an example, a second processing section with a maximum residence time of 12 minutes having a vertical conveyor segment with 6 carrier-receiving slots would travel at a rate of 2 minutes per slot increment (12 minutes÷6 slots=2 minutes per slot increment), where a slot increment corresponds to the movement required to move between a first slot and a second slot. In this example, each carrier-receiving slot skipped in the loading of the vertical carrier would reduce the maximum residence time by 2 minutes. Therefore, skipping 2 slots would provide an overall carrier residence time of 8 minutes (12 minutes−2 slots×2 minutes per slot=8 minutes).

By skipping two, three, or four or more carrier-receiving slots, for example, the residence time of the articles in the second processing section can be reduced even further—by a multiple of two, three, or four or more of the slot increment, respectively. Alternatively, the residence time of the carriers in the second processing section can again be increased by skipping fewer carrier-receiving slots when loading another carrier into the conveyor segment. In general, for a processing section having a maximum residence time of x minutes and n total carrier-receiving slots, skipping B carrier-receiving slots when loading carriers into the conveyor results in an overall reduction in residence time of $B(x/n)$, wherein B, and n are integers, B is 0 or higher, x is greater than 0, and n is at least 1. The residence time in the second processing zone for a given loading configuration is therefore equal to $x(1-B/n)$.

In certain implementations, the conveyor may be an indexing conveyor that moves, or "indexes," at regular periodic intervals and stops between those intervals. In such implementations, the skipping of carrier-receiving slots may be accomplished by adjusting the velocity of the conveyor during indexing. That is, more carrier-receiving slots may be skipped by increasing the velocity of the conveyor during the indexing step and fewer carrier-receiving slots may be skipped by decreasing the conveyor velocity. When the conveyor is operated at minimum velocity during indexing, no carrier-receiving slots are skipped and the conveyor is operated at full capacity. As a result, the articles in each carrier have the longest possible residence time within the processing zone. When the conveyor is operated at maximum velocity during indexing, the maximum number of carrier-receiving slots are skipped, the conveyor is operated at minimum capacity, and the articles in each carrier have the shortest possible residence time within the processing zone. By increasing or decreasing the carrier velocity during the indexing step, more or fewer carrier-receiving slots may be skipped.

Skipping one or more carrier-receiving slots when loading the vertical conveyor segment may transition the heating system from a first operating mode to a second operating mode. In certain embodiments, the ratio of the residence time of the carrier in the second processing section to the residence time of the carrier in the first processing section ($T_2:T_1$) during the second operating mode (or the ratio of the residence time of the carrier in the second processing section to the residence time of the carrier in the third processing section ($T_2:T_3$) during the second operating mode) can be at least about 5 percent different than the ratio of the residence time of the carrier in the second processing section to the residence time of the carrier in the first processing section ($T_2:T_1$) during the first operating mode (or the ratio of the residence time of the carrier in the second processing section to the residence time of the carrier in the third processing section ($T_2$:$T_3$) during the first operating mode). For example and without limitation, in some cases the ratio of the residence time of the carrier in the second processing section to the residence time of the carrier in the first processing section ($T_2$:$T_1$) during the second operating mode can be at least about 10 percent, at least about 15 percent, at least about 20 percent, at least about 25 percent, or at least about 30 percent different than the ratio of the residence time of the carrier in the second processing section to the residence time of the carrier in the first processing section ($T_2$:$T_1$) during the first operating mode. Similar ranges of values are applicable to the ratio of the residence time of the carrier in the second processing section to the residence time of the carrier in the third processing section ($T_2$:$T_3$) during the first and/or second operating modes.

When the transition from the first operating mode to the second operating mode includes skipping more carrier-receiving slots, the ratio of the residence time of the carrier in the second processing section to the residence time of the carrier in the first processing section ($T_2$:$T_1$) during the second operating mode can varied. For example and without limitation, the ratio of residence times may be at least about 5 percent, at least about 10 percent, at least about 15 percent, at least about 20 percent, at least about 25 percent, or at least about 30 percent higher than the ratio of the residence time of the carrier in the second processing section to the residence time of the carrier in the first processing section ($T_2$:$T_1$) during the first operating mode.

Conversely, when the transition from the first operating mode to the second operating mode includes skipping fewer carrier-receiving slots, the ratio of the residence time of the carrier in the second processing section to the residence time of the carrier in the first processing section ($T_2$:$T_1$) during the second operating mode can be, among other things, at least about 5 percent, at least about 10 percent, at least about 15 percent, at least about 20 percent, at least about 25 percent, or at least about 30 percent lower than the ratio of the residence time of the carrier in the second processing section to the residence time of the carrier in the first processing section ($T_2$:$T_1$) during the first operating mode.

Despite changes to the residence time of the loaded carriers within the first, second, and/or third processing zones, the average rate at which the articles are passed through each of these zones in the carriers can be substantially the same. For example and without limitation, in some cases the average rate at which the articles pass through the first, second, and third processing zones are within about 10 percent, within about 8 percent, within about 5 percent, within about 2 percent, or within about 1 percent of one another.

Referring again to FIGS. 1A-B, when the cooling section 108 includes a high-pressure cooling section 110 and a low-pressure cooling section 112, the system may also include a second pressure change section 115 located between the high- and low-pressure cooling sections 110, 112. The second pressure change section 115 may be configured in a similar manner as the first pressure change section 114, but may transition the carriers from a higher-pressure cooling 110 to a lower-pressure (or atmospheric pressure) cooling section 112. Various examples of suitable configurations of the pressure change section are described in the '590 Patent.

The low-pressure cooling section 112 within the cooling section 108 shown in FIGS. 1A-B may be configured to further cool the articles withdrawn from the higher-pressure cooling section 110. For example and without limitation, in some cases the low-pressure cooling section 112 may have a pressure of not more than about 15 psig, not more than about 10 psig, not more than about 8 psig, not more than about 6 psig, not more than about 5 psig, not more than about 3 psig, or not more than about 1 psig or may have a pressure at or near atmospheric. The low-pressure cooling section 112 may be configured to further reduce the temperature of the articles in the carriers by a particular amount. For example and without limitation, the low-pressure cooling section 112 may be configured to further reduce the temperature of the articles in the carriers by at least about 1° C., at least about 2° C., at least about 5° C., at least about 8° C., or at least about 10° C. and/or not more than about 20° C., not more than about 18° C., not more than about 15° C., not more than about 10° C., not more than about 8° C., or not more than about 5° C. The articles removed from the low-pressure cooling section 112 may have different average temperatures in different implementations of this disclosure. For example and without limitation, the articles removed from the low-pressure cooling section 112 may have an average temperature of at least about 20° C., at least about 22° C., at least about 25° C., or at least about 30° C. and/or not more than about 70° C., not more than about 65° C., not more than about 60° C., not more than about 55° C., not more than about 50° C., not more than about 45° C., or not more than about 40° C. The cooled, treated articles may be held for further thermal equilibration in an atmospheric cooling zone (not shown), or may be removed from the heating system for storage, transportation, and/or use.

Any suitable type of vessel may be used in the low-pressure cooling section 112. In some cases, the low-pressure cooling section 112 may include at least one vessel having an inlet side and an outlet side, similar to the vessel described previously for use in the preheat section 102. When such a vessel is used in the low-pressure cooling section 112, each of the inlet and outlet sides may include a respective conveyor segment for transporting the loaded carriers. In one implementation, the conveyor segments may be vertical conveyor segments that transport the loaded carriers upwardly and downwardly within the vessel, respectively. Additionally, the articles loaded into the carriers may also be contacted with a fluid when moving through the low-pressure cooling vessel. In certain implementations and without limitation, the temperature of the fluid may not more than about 50° C., not more than about 45° C., not more than about 40° C., not more than about 35° C., not more than about 30° C., or not more than about 27° C.

The fluid used to contact the articles may be in the form of a fluid bath in which the articles are submerged, a pressurized fluid spray, or a combination thereof. In some cases, the inlet side of the vessel used in the low-pressure cooling section 112 may be fluid filled, so that the articles in the carriers are at least partially submerged as the carriers move upwardly away from the carrier inlet, while the outlet side may include a plurality of fluid sprays for contacting the articles as the carriers move downwardly toward the carrier outlet. Additional features and functions of the conveyor segments and vessel used in the low-pressure cooling section 112 are similar to those described previously in the context of the preheat section 102.

Heating systems in accordance with the present disclosure can be commercial-scale heating systems capable of processing a large volume of articles in a relatively short time. In contrast to conventional retorts and other small-scale systems that utilize microwave energy to heat a plurality of articles, microwave heating systems as described herein can be configured to achieve varying overall production rates. For example and without limitation, implementations of the present disclosure may be configured to have an overall production rate of at least about 5 packages per minute, at least about 10 packages per minute, at least about 15 packages per minute per convey line, at least about 20 packages per minute per convey line, at least about 25 packages per minute per convey line, or at least about 30 packages per minute per convey line, measured as described in the '590 Patent.

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "including," "includes," and "include" have the same open-ended meaning as "comprising," "comprises," and "comprise."

As used herein, the terms "having," "has," and "have" have the same open-ended meaning as "comprising," "comprises," and "comprise."

As used herein, the terms "containing," "contains," and "contain" have the same open-ended meaning as "comprising," "comprises," and "comprise."

As used herein, the terms "a," "an," "the," and "said" mean one or more.

As used herein, the term "and/or," when used in a list of two or more items, means that any one of the listed items can be employed by itself or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

As generally used herein, the terms "about", "substantially", and "approximately" refer to an acceptable degree of error for the quantity measured, given the nature or precision of the measurement. Typical exemplary degrees of error may be within 20%, within 10%, or within 5% of a given value or range of values.

All numerical quantities stated herein are to be understood as being modified in all instances by the term "about" unless otherwise indicated. The numerical quantities disclosed herein are approximate and each numerical value is intended to mean both the recited value and a functionally equivalent range surrounding that value. At the very least, and not as an attempt to limit the application of the doctrine of equivalents to the scope of the claims, each numerical value should at least be construed in light of the number of reported significant digits and by applying ordinary rounding techniques. Notwithstanding the approximations of numerical quantities stated herein, the numerical quantities described in specific examples of actual measured values are reported as precisely as possible.

All numerical ranges stated herein include all sub-ranges subsumed therein. For example, ranges of "1 to 10" and "between 1 and 10" are intended to include all sub-ranges between and including the recited minimum value of 1 and the recited maximum value of 10.

All percentages and ratios are calculated by weight unless otherwise indicated. All percentages and ratios are calculated based on the total weight of the compound or composition unless otherwise indicated.

While the present disclosure has been described with reference to various implementations, it will be understood that these implementations are illustrative and that the scope of the present disclosure is not limited to them. Many variations, modifications, additions, and improvements are possible. More generally, embodiments in accordance with the present disclosure have been described in the context of particular implementations. Functionality may be separated or combined in blocks differently in various embodiments of the disclosure or described with different terminology. These and other variations, modifications, additions, and improvements may fall within the scope of the disclosure as defined in the claims that follow.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended thereto.

Numerous examples are provided herein to enhance understanding of the present disclosure. A specific set of statements are provided as follows. Such statements are intended merely as examples of potential implementations of the present disclosure and should not be viewed as limiting the scope of the disclosure.

Statement 1: A process for heating articles in a heating system, said process including: (a) passing a carrier loaded with an article through a vessel inlet and into a first vessel portion; (b) moving the loaded carrier in a first direction through said first vessel portion away from said inlet; (c) during at least a portion of said moving of step (b), contacting at least a portion of said articles in said loaded carrier with a first fluid medium; (d) moving the loaded carrier in a second direction opposite the first direction through a second vessel portion toward a vessel outlet; and (e) during at least a portion of said moving of step (d), contacting at least a portion of said articles in said loaded carrier with a second fluid medium.

Statement 2: The process of Statement 1 further including transferring the loaded carrier to said second vessel portion, wherein said second vessel portion is at least partially fluidly isolated from said first vessel portion.

Statement 3: The process of Statement 1 further including removing said loaded carrier from said second vessel portion via said vessel outlet.

Statement 4: The process of Statement 1, wherein said first direction and said second direction are vertical.

Statement 5: The process of Statement 4, wherein said first direction is vertically upward and said second direction is vertically downward.

Statement 6: The process of Statement 1, wherein said first vessel portion and said second vessel portion are chambers of a split-chamber vessel.

Statement 7: The process of Statement 1, wherein said contacting of step (c) includes discharging at least a portion of said first fluid medium from a plurality of spray nozzles as a fluid spray, and said article is contacted with said fluid spray during said moving of step (b).

Statement 8: The process of Statement 7, wherein said first vessel portion is at least partially filled with said first fluid medium forming a liquid bath, and wherein said contacting of step (c) includes at least partially submerging said article in said liquid bath during said moving of step (b).

Statement 9: The process of Statement 7, wherein at least one of said first vessel portion is not filled with said first fluid medium and said second vessel portion is not filled with said second fluid medium.

Statement 10: The process of Statement 1, wherein said contacting of step (e) includes discharging at least a portion of said second fluid medium from a plurality of spray nozzles as a fluid spray, wherein said articles are contacted with said fluid spray during said moving of step (d).

Statement 11: The process of Statement 10, wherein said second vessel portion is at least partially filled with said second fluid medium to form a liquid bath, and wherein said contacting of step (e) includes at least partially submerging said article in said second liquid during said moving of step (d).

Statement 12: The process of Statement 1, wherein said first fluid medium has a first temperature and said second fluid medium has a second temperature, said first temperature and said second temperature being within about 10° C. of each other.

Statement 13: The process of Statement 12, wherein said first temperature and said second temperature are each at least about 35° C.

Statement 14: The process of Statement 12, wherein said first temperature and said second temperature are each not more than about 45° C.

Statement 15: The process of Statement 1, wherein said first fluid medium has a first temperature and said second fluid medium has a second temperature, said first temperature being at least 30° C. higher than said second temperature.

Statement 16: The process of Statement 15, wherein said first temperature is at least 75° C.

Statement 17: The process of Statement 15, wherein said second temperature is not more than 40° C.

Statement 18: The process of Statement 1, wherein at least one of said first vessel portion and said second vessel portion is pressurized to at least 5 psig.

Statement 19: The process of Statement 1, wherein at least one of said first vessel potion and said second vessel portion has a pressure of not more than 5 psig.

Statement 20: The process of Statement 1 further including, loading a second article into a second carrier, and, subsequent to said passing of step (a), passing the second loaded carrier through said inlet and into said first vessel portion.

Statement 21: The process of Statement 20, wherein: at least a portion of said moving of step (b) includes simultaneously moving the loaded carrier and the second loaded carrier upwardly through said first vessel portion, and at least a portion of said moving of step (d) includes simultaneously moving the loaded carrier and the second loaded carrier downwardly through said second vessel portion.

Statement 22: The process of Statement 21 further including transferring the loaded carrier and the second loaded carrier one-by-one from said first vessel portion to said second vessel portion.

Statement 23: The process of Statement 21 further including: removing said loaded carrier from said second vessel portion via said vessel outlet; and subsequent to removing said loaded carrier, removing said second loaded from said second vessel portion via said vessel outlet.

Statement 24: The process of Statement 1 further including transferring the loaded carrier to said second vessel portion, wherein the loaded carrier is not contacted with said first fluid medium or said second fluid medium during said transferring.

Statement 25: The process of Statement 1 further including removing the loaded carrier from the second vessel portion via said vessel outlet and simultaneously introducing a second loaded carrier into said first vessel portion via said vessel inlet.

Statement 26: The process of Statement 1, wherein: said contacting of step (c) includes discharging at least a portion of said first fluid medium from a plurality of spray nozzles as a fluid spray and contacting said article with at least a portion of said fluid spray, said second vessel portion is at least partially filled with said second fluid medium to form a liquid bath, said contacting of step (e) includes submerging said article in said liquid bath, and said first fluid medium has a first temperature and said second fluid has a second temperature, each of said first temperature and said second temperature being at least 40° C.

Statement 27: The process of Statement 1, wherein: said contacting of step (c) includes submerging said article in a liquid bath of said first fluid, said contacting of said step (e) includes discharging at least a portion of said second fluid from a plurality of spray nozzles as a fluid spray and contacting said article with at least a portion of said fluid spray, and said first fluid has a first temperature and said second fluid medium has a second temperature, each of said first temperature and said second temperature being at least 40° C.

Statement 28: The process of Statement 1, wherein: said contacting of step (c) includes submerging said article in a first liquid bath of said first fluid medium, said contacting of step (e) includes submerging said article in a second liquid bath of said second fluid medium, and the first liquid bath has a first temperature and the second liquid bath has a second temperature, the first temperature being at least 20° C. higher than said second temperature.

Statement 29: The process of Statement 28, wherein said first temperature is at least 60° C. and said second temperature not more than 40° C.

Statement 30: The process of Statement 1, wherein a coldest portion of said article has a temperature of at least 60° C. when passed into said first vessel portion.

Statement 31: The process of Statement 1, wherein a coldest portion of said article has a temperature of not more than 35° C. when passed into said first vessel portion.

Statement 32: The process of Statement 1 further including, passing the loaded carrier along a convey line through a heating chamber and discharging microwave energy into said heating chamber during said passing, wherein at least a portion of the microwave energy is used to heat the article, and wherein said article is at least partially submerged in a liquid bath during said passing along said convey line.

Statement 33: The process of Statement 32, wherein the loaded carrier is passed through said heating section prior to said passing of step (a).

Statement 34: The process of Statement 32, wherein the loaded carrier is passed through said heating section subsequent to removing said carrier from said second vessel portion.

Statement 35: The process of Statement 1, wherein said heating system is a pasteurization or sterilization system.

Statement 36: The process of Statement 1, wherein said article includes packaged foodstuffs.

Statement 37: A heating system including: a heating chamber configured to heat articles using microwave energy, wherein said heating chamber includes a chamber adapted to be at least partially filled with a fluid medium; a conveyor for transporting carriers holding said articles through said heating chamber in a convey direction; and a vessel including: an inlet side and an outlet side, said inlet side and said outlet side being at least partially fluidly isolated from one another, a carrier inlet configured to receive one of said carriers into said inlet side; a carrier outlet configured to discharge one of said carriers out of said outlet side; a first convey segment located in said inlet side configured to move said carriers vertically away from said carrier inlet; and a second convey segment located in said outlet side configured to move said carriers vertically toward said carrier outlet.

Statement 38: The heating system of Statement 37, wherein said vessel is a split-chamber vessel, said inlet side includes a first chamber of said split-chamber vessel, and said outlet side includes a second chamber of said split-chamber vessel.

Statement 39: The heating system of Statement 37, wherein said first convey segment moves said carriers vertically upward and said second convey segment moves said carriers vertically downward.

Statement 40: The system of Statement 37, wherein: said first convey segment includes two pairs of support members spaced apart from one another in a direction parallel to said convey direction, said support members define a carrier receiving space therebetween, wherein each support member includes a plurality of carrier support members, and said carrier support members are arranged in an engaged configuration when said carrier support members are located within said carrier receiving space and are arranged in a disengaged configuration when said carrier support members are not located in said carrier receiving space.

Statement 41: The system of Statement 37, wherein said vessel includes at least one removable side panel.

Statement 42: The system of Statement 37, wherein said vessel is configured to be pressurized.

Statement 43: The system of Statement 37, wherein said vessel is an atmospheric vessel.

Statement 44: The system of Statement 37 further including a plurality of spray nozzles configured to discharge fluid medium toward said carriers in at least one of said inlet side and said outlet side.

Statement 45: The system of Statement 44, wherein said plurality of spray nozzles includes a first set of spray nozzles configured to discharge streams of fluid medium toward said carriers in said inlet side and a second set of spray nozzles configured to discharge streams of fluid medium toward said carriers in said outlet side.

Statement 46: The system of Statement 37, wherein the vessel is a first vessel, the system further including a second vessel including: a second inlet side and a second outlet side, said second inlet side and said second outlet side being at least partially fluidly isolated from one another; a second carrier inlet configured to receive one of said carriers at a time into said second inlet side; a second carrier outlet configured to discharge one of said carriers at a time out of said second outlet side; a third convey segment located in said second inlet side configured to move said carriers away from said second carrier inlet; and a fourth convey segment located in said second outlet side configured to move said carriers toward said second carrier outlet.

Statement 47: The system of Statement 46, wherein said first vessel is located upstream of said heating chamber and said second vessel is located downstream of said heating chamber.

Statement 48: The system of Statement 47 further including a pressure adjustment zone disposed between said heating section and said second vessel.

Statement 49: The system of Statement 48 further including a third vessel including: a third inlet side and a third outlet side, wherein said third inlet side and said third outlet side are at least partially fluidly isolated from one another; a third carrier inlet configured to receive one of said carriers at a time into said third inlet side; a third carrier outlet configured to discharge one of said carriers at a time out of said third outlet side: a fifth convey segment located in said third inlet side configured to move said carriers away from said third carrier inlet; and a sixth convey segment located in said third outlet side and to move said carriers toward said third carrier outlet.

Statement 50: The system of Statement 49 further including a low-pressure cooling chamber for cooling said articles in said carriers, said third vessel positioned between said heating section and said low-pressure cooling chamber.

Statement 51: The system of Statement 37, wherein said heating chamber is positioned upstream of said vessel.

Statement 52: The system of Statement 37, wherein said heating chamber is positioned downstream of said vessel.

Statement 53: The system of Statement 37 further including a pressure adjustment zone positioned between said heating chamber and said vessel.

Statement 54: The system of Statement 37, wherein said vessel includes a transfer section positioned between said inlet side and said outlet side, the transfer section configured to permit the transfer of one of said carriers at a time from said inlet side to said outlet side.

Statement 55: The system of Statement 54, wherein said transfer section includes at least one horizontal convey segment for moving one of said carriers from said inlet side to said outlet side.

Statement 56: A process for heating articles in a heating system, said process including: (a) preheating an article in a carrier in a preheat section; (b) after said preheating, heating the article in said carrier in a heating section, wherein at least a portion of said heating is performed using microwave energy; (c) passing said article in said carrier through a holding section, wherein a coldest temperature of said article is maintained at or above a hold temperature for a hold time in said holding section; and (d) cooling said article in said carrier in a cooling section, wherein at least a portion of one or more of said preheating, said passing, and said cooling are performed by moving said carrier at least one of upwardly and downwardly using at least one convey segment, and wherein said article is contacted by at least one fluid medium during said moving.

Statement 57: The process of Statement 56, wherein said at least one convey segment is a vertical convey segment.

Statement 58: The process of Statement 56, wherein said holding of step (c) is performed by moving said carrier through a first side of a vessel and contacting said article with warmed fluid medium and at least a portion of said cooling of step (d) is performed by moving said carrier through a second side of said vessel and contacting said article with cooled fluid medium.

Statement 59: The process of Statement 58, wherein said vessel is pressurized during said holding of step (c) and during at least a portion of said cooling of step (d) to greater than 5 psig.

Statement 60: The process of Statement 58, wherein said warmed fluid medium has a first temperature and said cooled fluid medium has a second temperature, said first temperature at least 20° C. higher than said second temperature.

Statement 61: The process of Statement 56, wherein said carrier is transferred from said first side to said second side of said vessel one at a time.

Statement 62: The process of Statement 56, wherein said preheating of step (a) is performed by moving said carrier vertically using one or more vertical convey segments disposed within a vessel.

Statement 63: The process of Statement 62, wherein said vessel during said preheating of step (a) has a pressure of less than 5 psig.

Statement 64: The process of Statement 62, wherein: said preheating of step (a) is performed by moving said carrier upwardly in a first side of said vessel and downwardly in a second side of said vessel, said article is contacted with a fluid spray including said at least one fluid medium in said first side, and said article is submerged in a liquid bath including said at least one fluid medium in said second side.

Statement 65: The process of Statement 56, wherein at least a portion of said cooling of step (d) is performed by moving said carrier vertically using one or more vertical convey segments disposed within a vessel.

Statement 66: The process of Statement 65, wherein said vessel has a pressure of less than 5 psig during said at least a portion of said cooling of step (d).

Statement 67: The process of Statement 65, wherein said at least one fluid medium has a temperature of not more than 35° C.

Statement 68: The process of Statement 65, wherein: said at least a portion of said cooling of step (d) is performed by moving said carrier upwardly in a first side of said vessel and downwardly in a second side of said vessel, said article is submerged in a liquid bath including a first fluid medium in said first side, and said article is contacted with a fluid spray including a second fluid medium in said second side.

Statement 69: The process of Statement 56, wherein said article is contacted by pressurized jets of said fluid medium during said moving of said carrier.

Statement 70: The process of Statement 56, wherein said article is at least partially submerged in a liquid bath of said fluid medium during said moving of said carrier.

Statement 71: The process of Statement 56, wherein said fluid medium has a temperature of at least 35° C.

Statement 72: The process of Statement 56, wherein said fluid medium has a temperature of not more than 35° C.

Statement 73: The process of Statement 56, wherein said article includes packaged foodstuffs.

Statement 74: The process of Statement 56, wherein said heating of step (b) is performed while said article is at least partially submerged in a liquid bath of a second fluid medium.

Statement 75: The process of Statement 56, wherein said heating of step (b) is sufficient to at least one of pasteurize or sterilize said article.

Statement 76: The process of Statement 56, wherein said heating system has an average product rate of at least 20 packages per minute equivalent.

We claim:

1. A process for heating articles in a heating system, said process comprises:
   (a) passing a carrier loaded with an article through an inlet of a vessel and into a first vessel portion of said vessel;
   (b) moving said carrier in a first direction through said first vessel portion away from said inlet;
   (c) during at least a portion of said moving of step (b), contacting at least a portion of said article in said carrier with a first fluid medium;
   (d) moving said carrier through a transfer section immediately downstream of said first vessel portion, wherein said transfer section transfers said carrier from the first vessel portion to a second vessel portion, and wherein said second vessel portion is immediately downstream of said transfer section;
   (e) moving said carrier in a second direction opposite said first direction through said second vessel portion toward an outlet of said vessel, said second vessel portion being at least partially fluidly isolated from said first vessel portion; and
   (f) in during at least a portion of said moving of step (d), contacting at least a portion of said article in said carrier with a second fluid medium,
   wherein all of steps (a)-(f) are performed either before or after applying microwave energy to said article in a heating chamber.

2. The process of claim 1 wherein said transfer section is at least partially fluidly isolated from each of said first vessel portion and said second vessel portion.

3. The process of claim 1, wherein said first direction and said second direction are vertical.

4. The process of claim 3, wherein said first direction is vertically upward and said second direction is vertically downward.

5. The process of claim 1 further comprising, loading a second article into a second carrier, and, subsequent to said passing of step (a), passing said second carrier through said inlet and into said first vessel portion, wherein:
   at least a portion of said moving of step (b) includes simultaneously moving said carrier and said second carrier upwardly through said first vessel portion, and
   at least a portion of said moving of step (d) includes simultaneously said carrier and said second carrier downwardly through said second vessel portion.

6. The process of claim 1, wherein:
   said contacting of step (c) includes submerging said article in a liquid bath of said first fluid medium,
   said contacting of step (f) includes discharging at least a portion of said second fluid medium from a plurality of spray nozzles as a fluid spray and contacting said article with at least a portion of said fluid spray, and
   said first fluid medium has a first temperature and said second fluid medium has a second temperature, each of said first temperature and said second temperature being at least 40° C.

7. The process of claim 1, wherein:
   said contacting of step (c) includes submerging said article in a first liquid bath of said first fluid medium,
   said contacting of step (f) includes submerging said article in a second liquid bath of said second fluid medium, and
   said first liquid bath has a first temperature and said second liquid bath has a second temperature, said first temperature being at least 20° C. higher than said second temperature.

8. The process of claim 1, further comprising:
   transporting said carrier into said heating chamber configured to heat said article using microwave energy, said heating chamber being at least partially filled with a third fluid medium; and
   applying said microwave energy to said article while said carrier is in said heating chamber and at least partially submerged within said third fluid medium.

9. The process of claim 1, wherein
   said inlet includes a first convey segment, said first convey segment including two pairs of support members spaced apart from one another in a direction parallel to said first direction, said support members defining a carrier receiving space therebetween, wherein each support member includes a plurality of carrier support members, and
   said carrier support members are arranged in an engaged configuration when said carrier support members are located within said carrier receiving space and are arranged in a disengaged configuration when said carrier support members are not located in said carrier receiving space.

10. The process of claim 1, wherein, at least one of said first fluid medium and said second fluid medium is discharged by a plurality of spray nozzles.

11. The process of claim 1, further comprising preheating said article in said carrier as said carrier is transported between said inlet and said outlet.

12. The process of claim 11, wherein said preheating comprises contacting said article with a fluid spray comprising said first fluid medium in said first vessel portion.

13. The process of claim 11, wherein said preheating comprises submerging said article in a liquid bath comprising said second fluid medium in said second vessel portion.

14. The process of claim 1, further comprising heating said article in said carrier using microwave energy as said carrier is transported between said inlet and said outlet.

15. The process of claim 1, further comprising cooling said article in said carrier as said carrier is transported between said inlet and said outlet.

16. The process of claim 15, wherein said cooling comprises contacting said article with cooled fluid medium.

17. The process of claim 1, further comprising maintaining a coldest temperature of said article at or above a hold temperature for a hold time as said carrier is transported between said inlet and said outlet.

18. The process of claim 17, wherein maintaining said coldest temperature of said article at or above said hold temperature comprises contacting said article with warmed fluid medium.

19. The process of claim 1, wherein said carrier is at least partially submerged in a liquid bath between said inlet and said outlet.

20. The process of claim 1, wherein at least one of said passing of step (a), said moving of step (b), and said moving of step (c) is performed using a conveyor having multiple convey segments.

* * * * *